US012167896B2

(12) United States Patent
Zheng et al.

(10) Patent No.: US 12,167,896 B2
(45) Date of Patent: Dec. 17, 2024

(54) SYSTEMS, METHODS, AND CATHETERS FOR ENDOVASCULAR TREATMENT OF A BLOOD VESSEL

(71) Applicant: TVA Medical, Inc., Franklin Lakes, NJ (US)

(72) Inventors: Peng Zheng, Chandler, AZ (US); Alexander W. Tessmer, Phoenix, AZ (US); Jeremy B. Cox, Salt Lake City, UT (US); Andrzej J. Chanduszko, Chandler, AZ (US); Michael Randall, Gilbert, AZ (US); Thomas Diffley Pate, Austin, TX (US)

(73) Assignee: TVA Medical, Inc., Franklin Lakes, NJ (US)

( * ) Notice: Subject to any disclaimer, the term of this patent is extended or adjusted under 35 U.S.C. 154(b) by 82 days.

(21) Appl. No.: 17/610,851

(22) PCT Filed: May 31, 2019

(86) PCT No.: PCT/US2019/034896
§ 371 (c)(1),
(2) Date: Nov. 12, 2021

(87) PCT Pub. No.: WO2020/242491
PCT Pub. Date: Dec. 3, 2020

(65) Prior Publication Data
US 2022/0280244 A1    Sep. 8, 2022

(51) Int. Cl.
*A61B 34/20* (2016.01)
*A61B 8/00* (2006.01)
(Continued)

(52) U.S. Cl.
CPC .............. *A61B 34/20* (2016.02); *A61B 8/085* (2013.01); *A61B 8/4209* (2013.01);
(Continued)

(58) Field of Classification Search
CPC ....... A61B 34/20; A61B 8/085; A61B 8/4209; A61B 8/4281; A61B 8/463; A61B 8/483; A61B 8/54; A61B 2034/2063
See application file for complete search history.

(56) References Cited

U.S. PATENT DOCUMENTS

| 4,919,133 | A | * | 4/1990 | Chiang .......... A61B 17/320783 |
| | | | | 606/159 |
| 5,383,460 | A | | 1/1995 | Jang et al. |

(Continued)

FOREIGN PATENT DOCUMENTS

| CN | 106344153 A | 1/2017 |
| JP | 2015504328 A | 2/2015 |

(Continued)

OTHER PUBLICATIONS

Japanese Office Action dated Dec. 15, 2022 pertaining to Japanese patent application 22021-570385.

*Primary Examiner* — Ashley K Buran
*Assistant Examiner* — Brooke Lyn Klein
(74) *Attorney, Agent, or Firm* — Dickinson Wright PLLC; Andrew D. Dorisio

(57) ABSTRACT

In one aspect, a system for endovascular treatment of a blood vessel includes a control unit, an ultrasound device, an actuator, and a catheter having a treatment portion. The ultrasound device is communicatively coupled to the control unit. The ultrasound device includes an ultrasound probe having a subject contact surface. The actuator is coupled to the ultrasound probe and is operable to move the subject contact surface of the ultrasound prove relative to a treatment zone of a subject. The control unit is configured to determine a position of the treatment portion of the catheter as the catheter is advanced through the blood vessel, and move the subject contact surface of the ultrasound probe relative to the treatment zone of the subject with the actuator (Continued)

to follow the position of the catheter as the catheter is advanced through the blood vessel.

12 Claims, 26 Drawing Sheets

(51) Int. Cl.
    *A61B 8/08*     (2006.01)
    *A61B 17/22*     (2006.01)
    *A61B 17/32*     (2006.01)

(52) U.S. Cl.
    CPC ............ *A61B 8/4281* (2013.01); *A61B 8/463* (2013.01); *A61B 8/483* (2013.01); *A61B 8/54* (2013.01); *A61B 17/22* (2013.01); *A61B 17/32* (2013.01); *A61B 2017/22069* (2013.01); *A61B 2034/2063* (2016.02)

(56) References Cited

U.S. PATENT DOCUMENTS

| | | | |
|---|---|---|---|
| 5,596,990 A * | 1/1997 | Yock | A61B 8/0833 |
| | | | 600/467 |
| 6,394,956 B1 | 5/2002 | Chandrasekaran et al. | |
| 6,669,709 B1 | 12/2003 | Cohn et al. | |
| 9,017,323 B2 | 4/2015 | Miller et al. | |
| 2004/0059280 A1 * | 3/2004 | Makower | A61B 17/12131 |
| | | | 606/108 |
| 2004/0147837 A1 * | 7/2004 | Macaulay | A61B 8/0833 |
| | | | 600/117 |
| 2007/0021738 A1 * | 1/2007 | Hasser | A61B 34/37 |
| | | | 606/1 |
| 2008/0221519 A1 | 9/2008 | Schwach et al. | |
| 2009/0187098 A1 | 7/2009 | Makower et al. | |
| 2009/0292204 A1 * | 11/2009 | Pansky | A61B 8/488 |
| | | | 600/439 |
| 2011/0301461 A1 * | 12/2011 | Anite | A61B 8/4209 |
| | | | 600/443 |
| 2013/0296704 A1 | 11/2013 | Magnin et al. | |
| 2014/0188028 A1 | 7/2014 | Brenneman et al. | |
| 2014/0288415 A1 * | 9/2014 | Forzoni | A61B 8/5284 |
| | | | 600/407 |
| 2015/0196309 A1 | 7/2015 | Matsubara et al. | |
| 2016/0008636 A1 * | 1/2016 | Warnking | A61B 8/445 |
| | | | 600/411 |
| 2016/0051323 A1 | 2/2016 | Stigall et al. | |
| 2016/0100840 A1 | 4/2016 | Brenneman et al. | |
| 2016/0199092 A1 * | 7/2016 | Patel | A61B 90/37 |
| | | | 606/159 |
| 2016/0324585 A1 * | 11/2016 | Noonan | A61B 90/37 |
| 2017/0071627 A1 | 3/2017 | Kellerman et al. | |
| 2017/0232272 A1 | 8/2017 | Perkins et al. | |
| 2017/0252006 A1 | 9/2017 | Tsuruno | |
| 2018/0333138 A1 | 11/2018 | Okumura | |
| 2020/0253668 A1 * | 8/2020 | Torjesen | A61B 90/37 |

FOREIGN PATENT DOCUMENTS

| | | |
|---|---|---|
| JP | 2017153846 A | 9/2017 |
| WO | 9729682 A1 | 8/1997 |
| WO | 2013067446 A1 | 5/2013 |
| WO | 2016081321 A2 | 5/2016 |
| WO | 2018211235 A1 | 11/2018 |

\* cited by examiner

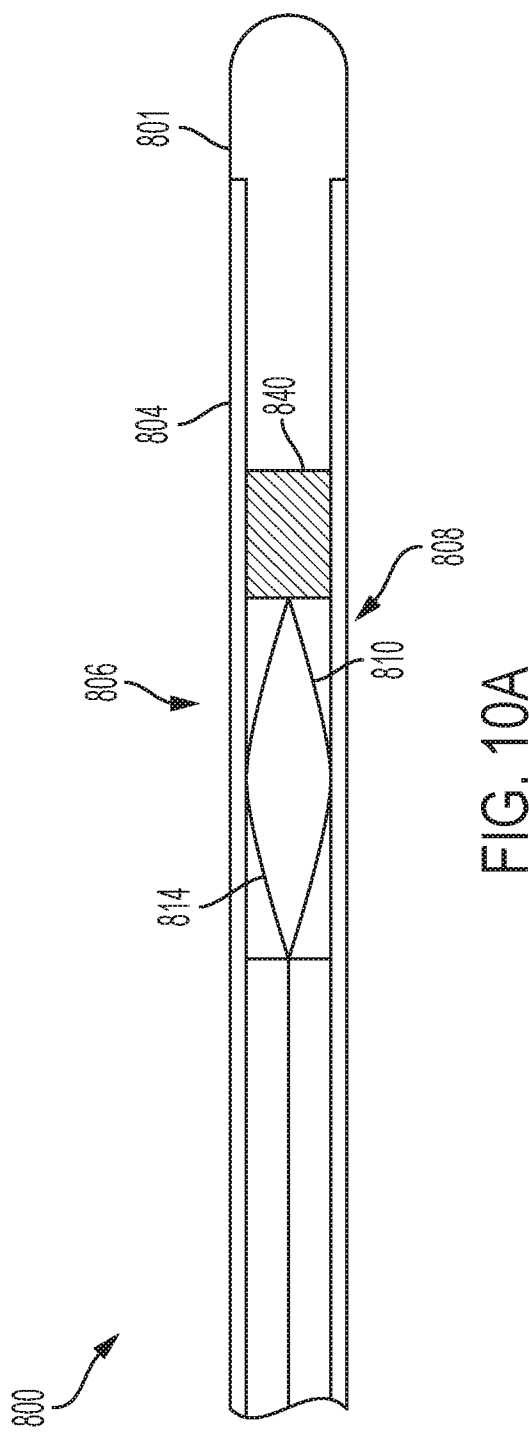
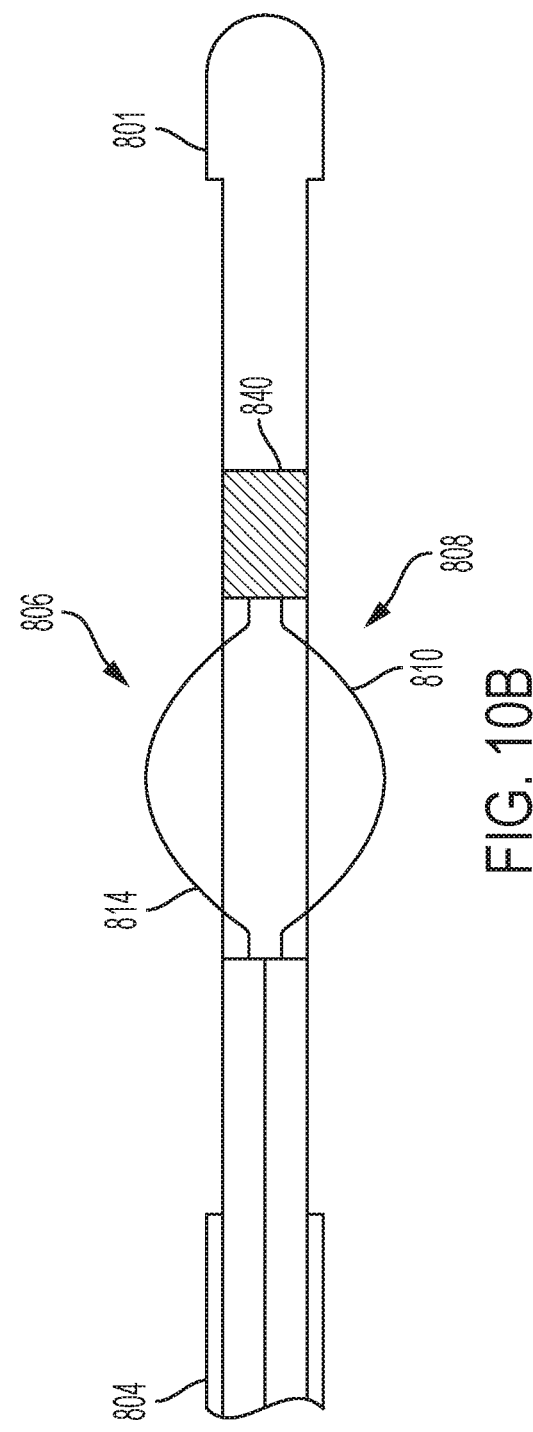

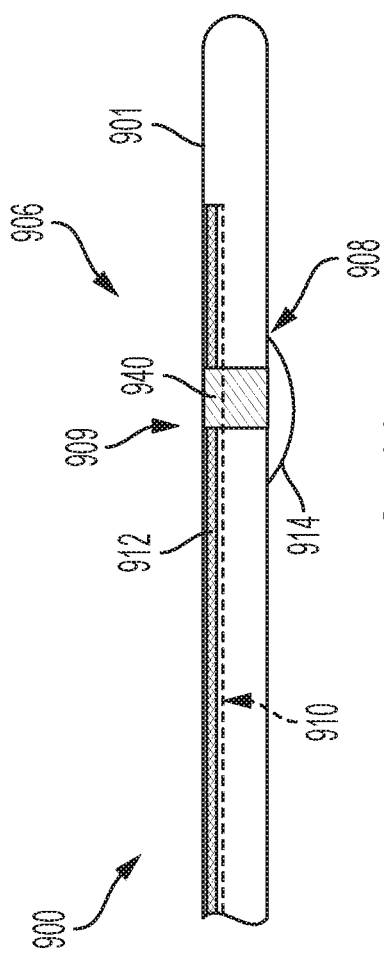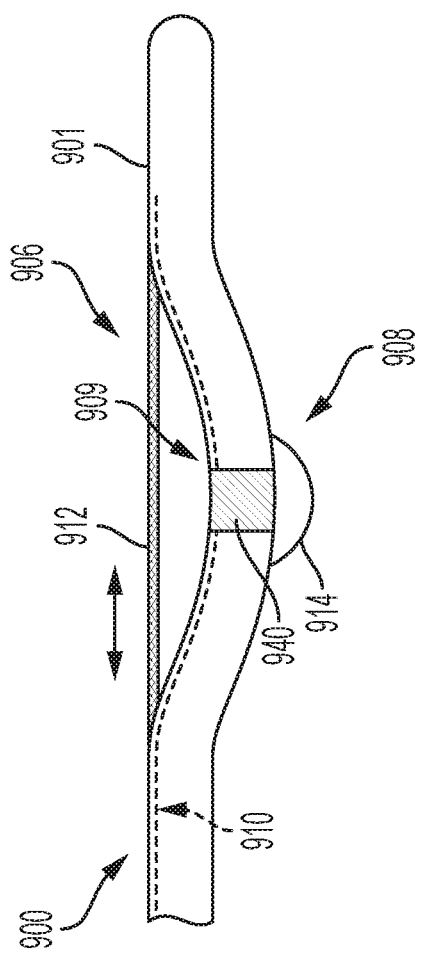

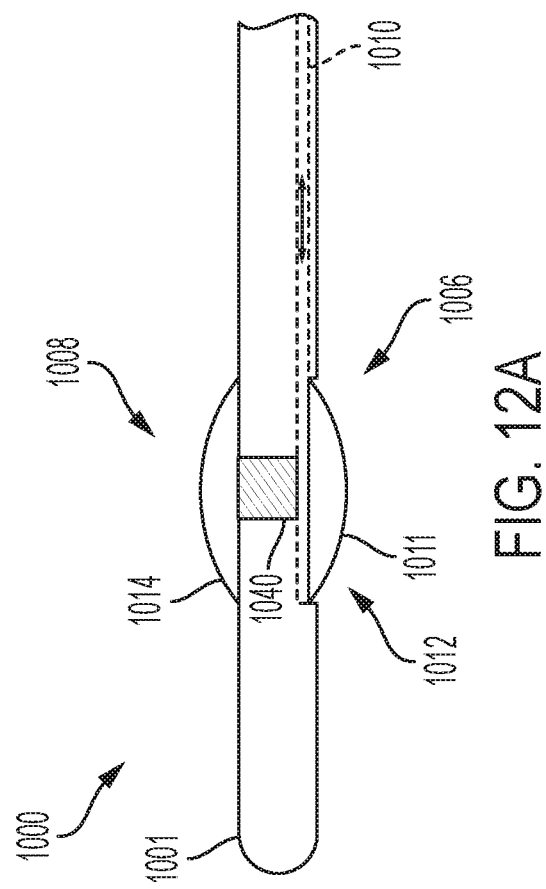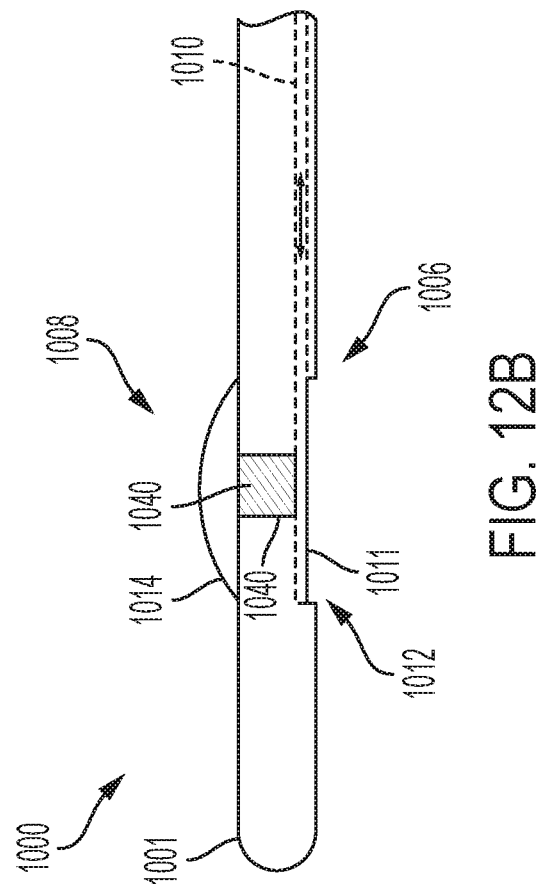

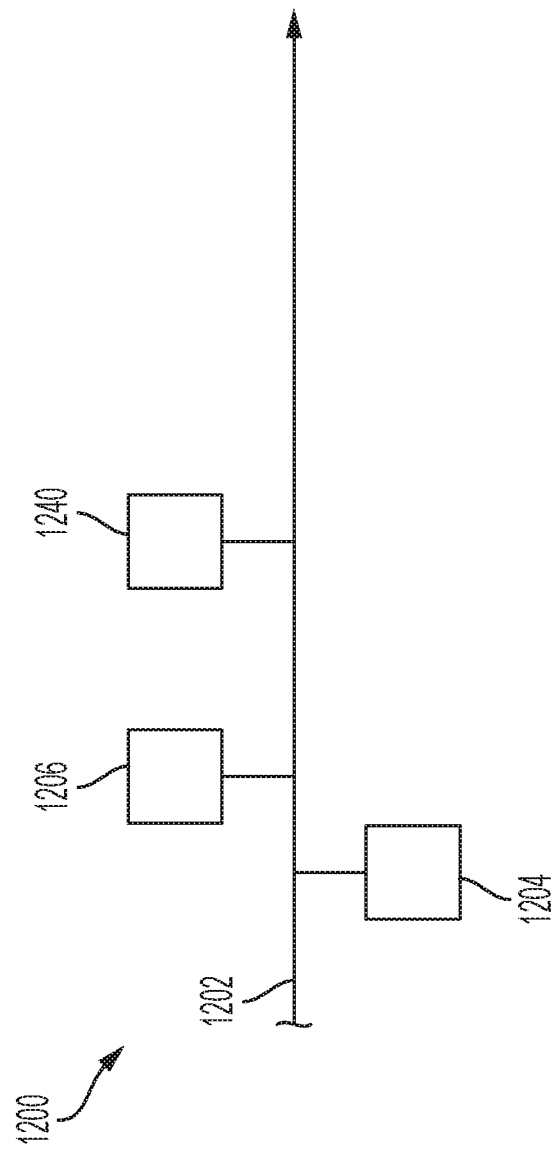

SYSTEMS, METHODS, AND CATHETERS FOR ENDOVASCULAR TREATMENT OF A BLOOD VESSEL

CROSS-REFERENCE TO RELATED APPLICATIONS

This application is a U.S. national phase of International Application No. PCT/US2019/034896, filed May 31, 2019, which is incorporated herein by reference in its entirety.

TECHNICAL FIELD

The present specification generally relates to systems, methods, and catheters for treatment of a blood vessel and, more specifically, systems, methods, and catheters for endovascular treatment of a blood vessel.

BACKGROUND

Endovascular treatments treat various blood vessel disorders from within the blood vessel using long, thin tubes called catheters, which are place inside the blood vessel to deliver the treatment. Endovascular treatments may include, but are not limited to, endovascular arteriovenous fistula (endoAVF) formations, arteriovenous (AV) treatments, and peripheral arterial disease (PAD) treatments. One of the most challenging aspects of endovascular treatment is proper alignment of a treatment portion of a catheter with the correct treatment location of the blood vessel. Additionally, treatments such as endovascular fistula formation may require two catheters positioned within adjacent blood vessels to form a fistula therebetween. However, alignment and position of two separate catheters may also be difficult/cumbersome for a practitioner.

Additionally, imaging systems for visualizing catheter alignment within blood vessels may also provide numerous hurdles to overcome. In particular fluoroscopy equipment is very expensive, accordingly such equipment might not be available outside of an operating room or in rural locations. Moreover, repeated use of fluoroscopy equipment may introduce radiation not only to the patient but also to the physician. Overtime, such repeat exposure may impact the physician's health. Additionally, contrast dyes used in fluoroscopy may not be suitable for patients with certain medical conditions (e.g., chronic kidney disease).

Accordingly, a need exists for alternative systems, methods, and catheters for endovascular treatment of a blood vessel that improve alignment techniques of the catheter within the blood vessel, and or catheters for endovascular treatment of a blood vessel that allow for simpler delivery of treatment to the blood vessel.

SUMMARY

The present embodiments address the above referenced problems. In particular, the present disclosure is directed to systems, methods, and catheters to improved visualization and alignment techniques for delivery of treatments (e.g., fistula formation) using one or more catheters to a blood vessel. Additionally, some embodiments are directed to single catheter systems which may reduce complexity of current two catheter systems.

In a first aspect, a system for endovascular treatment of a blood vessel includes a control unit, an ultrasound device, an actuator, and a catheter having a treatment portion. The ultrasound device is communicatively coupled to the control unit. The ultrasound device includes an ultrasound probe having a subject contact surface. The actuator is coupled to the ultrasound probe and is operable to move the subject contact surface of the ultrasound prove relative to a treatment zone of a subject. The control unit is configured to determine a position of the treatment portion of the catheter as the catheter is advanced through the blood vessel, and move the subject contact surface of the ultrasound probe relative to the treatment zone of the subject with the actuator to follow the position of the catheter as the catheter is advanced through the blood vessel.

In a second aspect, the present disclosure includes a system according to the first aspect, further including one or more user input devices communicatively coupled to the control unit, wherein the control unit is further configured to: received user input from the one or more user input device, and switch to a manual operation mode from an automatic following mode to allow for manual control of movement of the ultrasound probe based on input from the one or more user input devices.

In a third aspect, the present disclosure includes a system according to any preceding aspect, further including a display communicatively coupled to the control unit wherein the control unit is further configured to display one or more ultrasound images with the display in real time as the catheter is advanced through the blood vessel.

In a fourth aspect, the present disclosure includes a system according to the third aspect, wherein the control unit is further configured to determine an orientation of the treatment portion of the catheter within the blood vessel and output an indication of the orientation of the treatment portion of the catheter with the display.

In a fifth aspect, the present disclosure includes a system according to any preceding aspect, wherein the ultrasound device is a 3D ultrasound device and the control unit is configured to display two or more of a frontal plane ultrasound image, an axial plane ultrasound image, and sagittal plane ultrasound image.

In a sixth aspect, the present disclosure includes a system according to any preceding aspect, wherein the ultrasound device is a 3D ultrasound device and the control unit is configured to recognize one or more vessels within an ultrasound image of the ultrasound device and display a 3D model of the one or more vessels on the display.

In a seventh aspect, the present disclosure includes a system according to any preceding aspect, further including a media bath configured to be placed over a treatment zone of a subject, wherein the ultrasound device moves within the media bath.

In an eighth aspect, the present disclosure includes a system according to the seventh aspect, wherein the media bath comprises a flexible subject interface, wherein the flexible subject interface conforms to a shape of the treatment zone of the subject.

In a ninth aspect, the present disclosure includes a system according to the seventh aspect or the eighth aspect, wherein the media bath comprises a housing comprising a track, wherein the ultrasound device is moveable along the track.

In a tenth aspect, the present disclosure includes a system according to any preceding aspect, wherein the catheter comprises a housing, a cutting device, and a biasing mechanism coupled to the housing of the catheter and configured to bias the cutting device against a wall of the blood vessel.

In an eleventh aspect, the present disclosure includes a system according to the tenth aspect, wherein the biasing mechanism is a balloon.

In a twelfth aspect, the present disclosure includes a system according to the tenth aspect, wherein the biasing mechanism is an expandable cage.

In a thirteenth aspect, the present disclosure includes a system according to any of the tenth through twelfth aspects, wherein the biasing mechanism comprises one or more expandable wires moveable between a collapsed position and an expanded position wherein at least a portion of the one or more expandable wire are spaced from an outer wall of the housing of the catheter.

In a fourteenth aspect, the present disclosure includes a system according to any of the tenth through the thirteenth aspects, wherein the catheter comprises one or more echogenic markers, wherein the one or more echogenic markers indicate a rotational alignment of cutting device of the catheter.

In a fifteenth aspect, a system for endovascular treatment of a blood vessel includes a control unit, an imaging device, a display, and a catheter having a treatment portion. The imaging device and the display are communicatively coupled to the control unit. The control unit is configured to display an image of the blood vessel, determine a rotational orientation of the treatment portion of the catheter within the blood vessel, and output an indication of the rotational orientation of the treatment portion of the catheter with the display.

In a sixteenth aspect, the present disclosure includes a system according to the fifteenth aspect, wherein the indication comprises an overlay projected over the image of the blood vessel, the overlay providing an indicator of the rotational orientation of the treatment portion of the catheter.

In a seventeenth aspect, the present disclosure includes a system according to the fifteenth aspect or the sixteenth aspect, wherein the imaging device is an ultrasound imaging device.

In an eighteenth aspect, the present disclosure includes a system according to any of the fifteenth aspect through the seventeenth aspect, wherein the imaging device is an intravascular imaging device.

In a nineteenth aspect, the present disclosure includes a system according to any of the fifteenth aspect through the eighteenth aspect, wherein the imaging device is coupled to the catheter at a position distal to the treatment portion.

In a twentieth aspect, the present disclosure includes a system according to any of the fifteenth aspect through the nineteenth aspect, wherein the imaging device is coupled to the catheter at a position proximal to the treatment portion.

In a twenty-first aspect, the present disclosure includes a system according to any of the fifteenth aspect through the twentieth aspect, wherein the imaging device is a 3D ultrasound device and the control unit is configured to display two or more of a frontal plane ultrasound image, an axial plane ultrasound image, and sagittal plane ultrasound image with the display.

In a twenty-second aspect, the present disclosure includes a system according to any of the fifteenth aspect through the twenty-first aspect, wherein the ultrasound device is a 3D ultrasound device and the control unit is configured to recognize one or more vessels within an ultrasound image of the ultrasound device and display a 3D model of the one or more vessels on the display.

In a twenty-third aspect, the present disclosure includes a system according to any of the fifteenth aspect through the twenty-second aspect, wherein the catheter comprises a housing, wherein the treatment portion of the catheter is coupled to the housing of the catheter at a first radial position.

In a twenty-fourth aspect, the present disclosure includes a system according to the twenty-third aspect, wherein the catheter further comprises a biasing mechanism coupled to the housing of the catheter, the biasing mechanism configured to bias the treatment portion of the catheter toward a wall of the blood vessel.

In a twenty-fifth aspect, the present disclosure includes a system according to the twenty-fourth aspect, wherein the biasing mechanism is coupled to the housing of the catheter proximate to the treatment portion.

In a twenty-sixth aspect, the present disclosure includes a system according to any of the fifteenth aspect through the twenty-fifth aspect, wherein the treatment portion comprises a cutting device.

In a twenty-seventh aspect, the present disclosure includes a system according to any of the twenty-fourth aspect through the twenty-sixth aspect when depending on the twenty-fourth aspect, wherein the biasing mechanism is a balloon.

In a twenty-ninth aspect, the present disclosure includes a system according to any of the twenty-fourth aspect through the twenty-sixth aspect when depending on the twenty-fourth aspect, wherein the biasing mechanism comprises one or more expandable wires moveable between a collapsed position and an expanded position wherein at least a portion of the one or more expandable wire are spaced from an outer wall of the housing of the catheter.

In a thirtieth aspect, the present disclosure includes a system according to any of the fifteenth aspect through the twenty-ninth aspect, wherein the catheter comprises one or more echogenic markers, wherein the one or more echogenic markers indicate a rotational alignment of cutting device of the catheter.

In a thirty-first aspect, the present disclosure includes a catheter for endovascular treatment of a blood vessel includes a housing, a treatment portion coupled to the housing, an intravascular imaging device coupled to the housing, and a biasing mechanism coupled to the housing. The biasing mechanism is configured to contact a wall of the blood vessel to bias the treatment portion into contact with the wall of the blood vessel.

In a thirty-second aspect, the present disclosure includes a system according to the thirty-first aspect, wherein the biasing mechanism is configured to contact a first radial portion of the wall of the blood vessel to bias the treatment portion toward a second radial portion of the wall of the blood vessel opposite the first radial portion.

In a thirty-third aspect, the present disclosure includes a system according to the thirty-first aspect or the thirty-second aspect, wherein the intravascular imaging device is coupled to the housing of the catheter at a position distal to the treatment portion.

In a thirty-fourth aspect, the present disclosure includes a system according to the thirty-first aspect or the thirty-second aspect, wherein the intravascular imaging device is coupled to the housing of the catheter at a position proximal to the treatment portion.

In a thirty-fifth aspect, the present disclosure includes a system according to the thirty-first aspect or the thirty-second aspect, wherein the intravascular imaging device is coupled to the housing of the catheter at a position longitudinally aligned with the treatment portion of the catheter.

In a thirty-sixth aspect, the present disclosure includes a system according to any of the thirty-first aspect through the thirty-fifth aspect, wherein the treatment portion comprises an electrode comprising an arc that extends from the housing, and wherein the intravascular imaging device is positioned so as to capture image data of a cross-section of the catheter taken perpendicular to a longitudinal direction of the catheter at a apex of the arc.

In a thirty-seventh aspect, the present disclosure includes a system according to any of the thirty-first aspect through the thirty-sixth aspect, wherein the intravascular imaging device is positioned longitudinally within the treatment portion of the catheter.

In a thirty-eighth aspect, the present disclosure includes a system according to any of the thirty-first aspect through the thirty-seventh aspect, wherein the treatment portion comprises an electrode, wherein the intravascular imaging device is positioned longitudinally with the treatment portion of the catheter, so as to capture image data of a cross-section of the electrode.

In a thirty-ninth aspect, the present disclosure includes a system according to any of the thirty-first aspect through the thirty-eighth aspect, wherein the biasing mechanism is coupled to the housing of the catheter proximate to the treatment portion.

In a fortieth aspect, the present disclosure includes a system according to any of the thirty-first aspect through the thirty-ninth aspect, wherein the treatment portion comprises a cutting device.

In a forty-first aspect, the present disclosure includes a system according to any of the thirty-first aspect through the fortieth aspect, wherein the biasing mechanism is a balloon.

In a forty-second aspect, the present disclosure includes a system according to any of the thirty-first aspect through the fortieth aspect, where in the biasing mechanism is an expandable cage.

In a forty-third aspect, a method for endovascular treatment of a blood vessel includes advancing a catheter within the blood vessel to a treatment location of the blood vessel, aligning a treatment portion of the catheter with the treatment location of the blood vessel, and deploying the catheter with a biasing mechanism coupled to a body of the catheter. The biasing mechanism is configured to contact a first radial portion of the blood vessel to bias the treatment portion of the catheter toward the treatment location of the blood vessel opposite the first radial portion.

In a forty-fourth aspect, the present disclosure includes a method according to the forty-third aspect, wherein the treatment portion comprises a cutting device.

In a forty-fifth aspect, the present disclosure includes a method according to the forty-third aspect or the forty-fourth aspect, wherein the biasing mechanism is a balloon.

In a forty-sixth aspect, the present disclosure includes a method according to the forty-third aspect or the forty-fourth aspect, where in the biasing mechanism is an expandable cage.

In a forty-seventh aspect, the present disclosure includes a method according to any of the forty-third aspect through the forty-sixth aspect, wherein the biasing mechanism is coupled to the housing of the catheter proximate to the treatment portion.

In a forty-eighth aspect, the present disclosure includes a method according to any of the forty-third aspect through the forty-seventh aspect, further including determining a position of the treatment portion of the catheter as the catheter is advanced through the blood vessel with a control unit, moving an imaging device with an actuator to follow the position of the catheter as the catheter is advanced through the blood vessel, and displaying one or more images from the imaging device with a display in real time as the catheter is advanced through the blood vessel.

In a forty-ninth aspect, the present disclosure includes a method according to any of the forty-third aspect through the forty-eighth aspect, further including capturing image data with an imaging device coupled to the catheter, and displaying image data from the imaging device with a display in real time as the catheter is advanced through the blood vessel.

In a fiftieth aspect, the present disclosure includes a method according to any of the forty-third aspect through the forty-ninth aspect, further including determining a rotational alignment of the catheter, and displaying an indication of the rotational alignment of the catheter with the display.

In a fifty-first aspect, the present disclosure includes a method according to any of the forty-third aspect through the fiftieth aspect, further including determining a rotational alignment of the treatment portion of the catheter, and displaying an indication of the rotational alignment of the treatment portion of the catheter with the display.

In a fifty-second aspect, the present disclosure includes a method according to any of the forty-third aspect through the fifty-first aspect, further including automatically adjusting the imaging device to automatically focus the imaging device on the treatment portion of the catheter to adjust image quality using one or more location sensors and/or echogenic markers.

In a fifty-third aspect, the present disclosure includes a system according to any of the fifteenth through thirtieth aspect, wherein the imaging device is an ultrasound device, and the control unit is configured to: recognize an arterial blood flow using a Doppler functionality of the ultrasound device; recognize a venous blood flow using the Doppler Functionality of the ultrasound device; and display a blood vessel map based on the arterial blood flow and the venous blood flow.

In a fifty-fourth aspect, the present disclosure includes a system according to the fifty-third aspect, wherein the arterial blood flow is depicted as a first color and the venous blood flow is depicted as a second color different from the first color in the blood vessel map.

In a fifty-fifth aspect, the present disclosure includes a system according to the fifty-third aspect or the fifty-fourth aspect, wherein the control unit is configured to recognize fistula creation by identifying blood flow between an adjacent artery and vein using the Doppler functionality of the ultrasound device.

In a fifty-sixth aspect, the present disclosure include a control unit for endovascular treatment of a blood vessel with one or more catheters. The control unit includes one or more process and one or more memory modules communicatively coupled to the one or more processors. The control unit is configured to be communicatively coupled to an imaging device and a display. When the one or more processors execute logic stored on the one or more memory modules, the control unit displays the image data from the imaging device of a blood vessel, determines a rotational orientation of a treatment portion of a catheter within a blood vessel, and outputs an indication of the rotational orientation of the treatment portion of the catheter with the display.

In a fifty-seventh aspect, the present disclosure includes a control unit according to the fifty-sixth aspect, wherein the indication comprises an overlay projected over the image of the blood vessel, the overlay providing an indicator of a rotational orientation of the treatment portion of the catheter.

In a fifty-eighth aspect, the present disclosure includes a control unit according to the fifty-sixth aspect or the fifty-seventh aspect, wherein the imaging device is an ultrasound imaging device.

In a fifty-ninth aspect, the present disclosure includes a control unit according to any of the fifty-sixth aspect through the fifty-eighth aspect, wherein the imaging device is an intravascular imaging device.

In a sixtieth aspect, the present disclosure includes a control unit according to any of the fifty-sixth aspect through the fifty-ninth aspect, wherein the imaging device is coupled to the catheter at a position distal to the treatment portion.

In a sixty-first aspect, the present disclosure includes a control unit according to any of the fifty-sixth aspect through the fifty-ninth aspect, wherein the imaging device is coupled to the catheter at a position proximal to the treatment portion.

In a sixty-second aspect, the present disclosure includes a control unit according to any of the fifty-sixth aspect through the sixty-first aspect, wherein the imaging device is a 3D ultrasound device and the control unit is configured to display two or more of a frontal plane ultrasound image, an axial plane ultrasound image, and sagittal plane ultrasound image with the display.

In a sixty-third aspect, the present disclosure includes a control unit according to any of the fifty-sixth aspect through the sixty-second aspect, wherein the ultrasound device is a 3D ultrasound device and the control unit is configured to recognize one or more vessels within an ultrasound image of the ultrasound device and display a 3D model of the one or more vessels on the display.

In a sixty-fourth aspect, the present disclosure includes a control unit according to any of the fifty-sixth aspect through the sixty-third aspect, wherein the control unit is configured to be communicatively coupled to one or more location sensors coupled to the catheter, the one or more location sensors outputting a location signal indicative of a location of the treatment portion, wherein the control unit is configured to determine a location of the treatment portion based on the signal from the one or more location sensors.

In a sixty-fifth aspect, the present disclosure includes a control unit according to any of the fifty-sixth aspect through the sixty-fourth aspect, wherein the imaging device is an ultrasound device, and the control unit is configured to: recognize an arterial blood flow using a Doppler functionality of the ultrasound device; recognize a venous blood flow using the Doppler functionality of the ultrasound device; and display a blood vessel map based on the arterial blood flow and the venous blood flow.

In a sixty-sixth aspect, the present disclosure includes a control unit according to the sixty-fifth aspect, wherein the arterial blood flow is depicted as a first color and the venous blood flow is depicted as a second color different from the first color in the blood vessel map.

In a sixty-seventh aspect, the present disclosure includes a control unit according to any of the fifty-sixth aspect through the sixty-sixth aspect, herein the control unit is configured to recognize fistula creation by identifying blood flow between an adjacent artery and vein using the Doppler functionality of the ultrasound device.

In a sixty-eighth aspect, the present disclosure includes a control unit for endovascular treatment of a blood vessel using one or more catheters. The control unit includes one or more processors and one or more memory modules communicatively coupled to the one or more processors. The control unit is configured to be communicatively coupled to an ultrasound probe having a subject contact surface, and an actuator coupled to the ultrasound probe. When the one or more processors execute logic stored on the one or more memory modules, the control unit determines a position of a treatment portion of a catheter as the catheter is advanced through the blood vessel; and moves a subject contact surface of the ultrasound probe relative to the treatment zone of the subject with the actuator to follow the position of the catheter as the catheter is advanced through the blood vessel.

In a sixty-ninth aspect, the present disclosure includes a control unit according to the sixty-eight aspect, wherein the control unit is configured to be communicatively coupled to one or more user input devices, wherein the control unit is further configured to: receive user input from the one or more user input devices; and switch to a manual operation mode from an automatic following mode to allow for manual control of movement of the ultrasound probe based on input from the one or more user input devices.

In a seventieth aspect, the present disclosure includes a control unit according to the sixty-eight aspect or the sixty-ninth aspect, wherein the control unit is configured to be communicatively coupled to a display, wherein the control unit is further configured to: display one or more ultrasound images with the display in real time as the catheter is advanced through the blood vessel.

In a seventy-first aspect, the present disclosure includes a control unit according to any of the sixty-eighth aspect through the seventieth aspect, wherein the control unit is further configured to determine an orientation of the treatment portion of the catheter within the blood vessel and output an indication of the orientation of the treatment portion of the catheter with the display.

In a seventy-second aspect, the present disclosure includes a control unit according to any of the sixty-eighth aspect through the seventy-first aspect, wherein the ultrasound device is a 3D ultrasound device and the control unit is configured to display two or more of a frontal plane ultrasound image, an axial plane ultrasound image, and sagittal plane ultrasound image.

In a seventy-third aspect, the present disclosure includes a control unit according to any of the sixty-eighth aspect through the seventy-second aspect, wherein the ultrasound device is a 3D ultrasound device and the control unit is configured to recognize one or more vessels within an ultrasound image of the ultrasound device and display a 3D model of the one or more vessels on the display.

In a seventy-fourth aspect, the present disclosure includes a control unit according to any of the sixty-eight aspect through the seventy-third aspect, wherein the catheter comprises one or more echogenic markers, and the control unit is configured to determine a rotational orientation of the catheter based on recognition of the one or more echogenic markers.

In a seventy-fifth aspect, the present disclosure includes a control unit according to any of the sixty-eight aspect through the seventy-fourth aspect, wherein the control unit is configured to be communicatively coupled to one or more location sensors coupled to the catheter, the one or more location sensors outputting a location signal indicative of a location of the treatment portion, wherein the control unit is configured to determine a location of the treatment portion based on the signal from the one or more location sensors.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

FIG. 10A depicts a cross-section of a single catheter system in an un-expanded state, according to one or more embodiments shown and described herein;

FIG. 10B depicts a cross-section of the single catheter system of FIG. 10A in an expanded state, according to one or more embodiments shown and described herein;

FIG. 11A depicts a single catheter system in an un-expanded state, according to one or more embodiments shown and described herein;

FIG. 11B depicts the single catheter system of FIG. 11A in an expanded state, according to one or more embodiments shown and described herein;

FIG. 12A depicts a single catheter system in an un-expanded state, according to one or more embodiments shown and described herein;

FIG. 12B depicts a single catheter system in an un-expanded state, according to one or more embodiments shown and described herein;

FIG. 15 schematically depicts communications between various modules of a system for endovascular treatment of a blood vessel, according to one or more embodiments shown and described herein;

DETAILED DESCRIPTION

Figure 1:
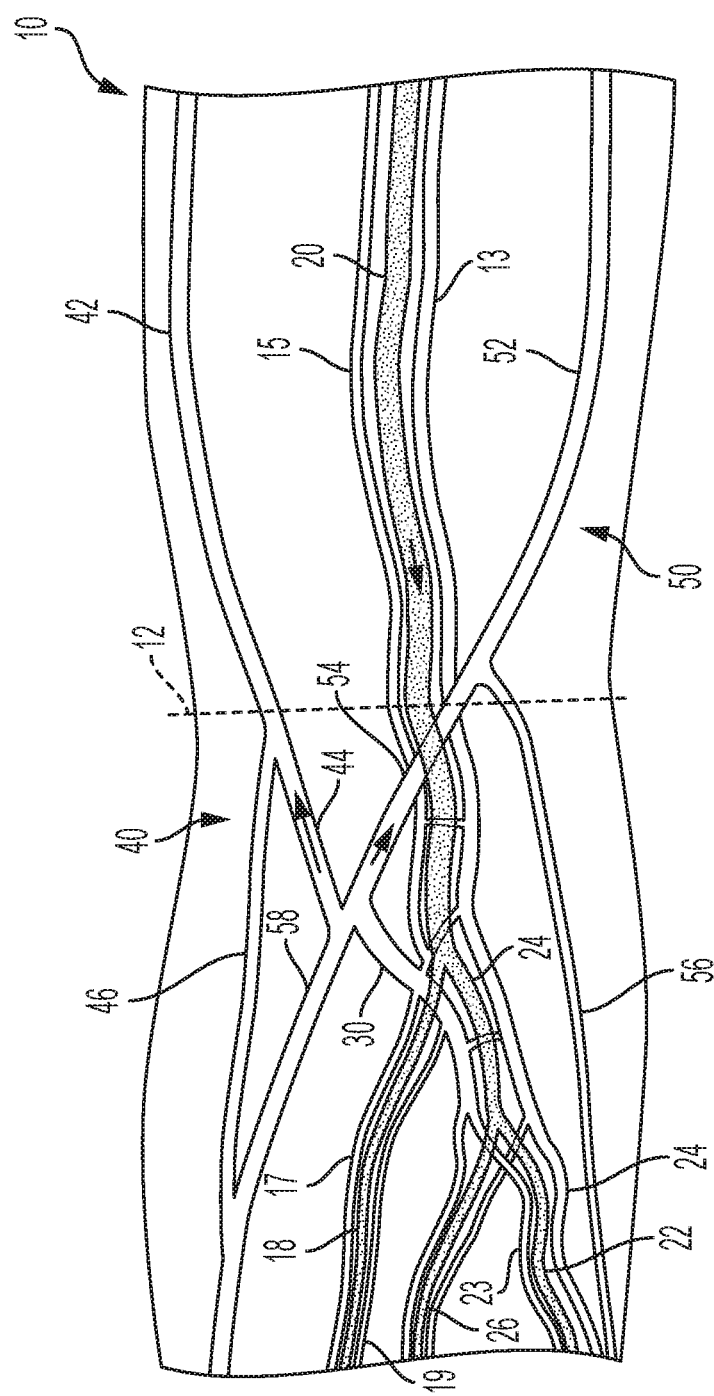
FIG. 1 is an illustrative depiction of the vascular anatomy of an arm in which an endovascular treatment may be delivered, according to one or more embodiments shown and described herein.

Embodiments as described herein are directed the systems, methods, and catheters for endovascular treatment of a blood vessel. Endovascular treatments may include but are not limited to fistula formation, vessel occlusion, angioplasty, thrombectomy, atherectomy, crossing, drug coated balloon angioplasty, stenting (uncovered and covered), lytic therapy. Accordingly, while various embodiments are directed to fistula formation between two blood vessels, other vascular treatments are contemplated and possible. The figures generally depict various systems, methods, and devices that allow an operator to visualize and determine when a catheter has reached the correct location to provide treatment to the blood vessel (e.g., form a fistula between adjacent blood vessels). In particular, determining when a catheter has reached a desired location for treatment may be very challenging to an operator. In particular, visualization systems (e.g., ultrasound, fluoroscopy, etc.) may include the need of equipment that may be difficult to control while also controlling advancement of one or more catheter's through a vasculature of a patient. Additionally, such equipment may be expensive, leading treatment facilities to only include such visualization systems in operating rooms or the like. Accordingly, systems as described herein will make visualization easier and/or more accessible for various applications.

Additionally, using two catheters to form a fistula or otherwise provide a treatment (e.g., advancing a wire from one blood vessel to another) has been described in U.S. Pat. No. 9,017,323, entitled "Devices and Methods for Forming Fistula," filed Nov. 16, 2011, hereby incorporated by reference in its entirety; U.S. Pat. No. 9,486,276, entitled "Devices and Methods for Fistula Formation," filed Oct. 11, 2013, hereby incorporated by reference in its entirety; U.S. Patent Application Publication No. 2014/0276335, entitled Fistula Formation Devices and Methods Therefor," filed Mar. 14, 2014, hereby incorporated by reference in its entirety; U.S. Patent Application Publication No. 2015/0258308, filed Mar. 13, 2015, hereby incorporated by reference in its entirety; U.S. patent application Ser. No. 15/019,962, entitled Methods for Treating Hypertension, Filed Feb. 9, 2016, hereby incorporated by reference in its entirety; U.S. Patent Application Publication No. 2017/0202616, entitled "Devices and Methods for Forming a Fistula," filed Jan. 15, 2017, hereby incorporated by reference in its entirety; U.S. Patent Application Publication No. 2017/0202603, entitled "Systems and Methods for Increasing Blood Flow," Filed Jan. 15, 2017, hereby incorporated by reference in its entirety; U.S. patent application Ser. No. 16/024,241, entitled "Systems and Methods for Adhering Vessels," filed Jun. 29, 2018, hereby incorporated by reference in its entirety; and U.S. patent application Ser. No. 16/024,345, entitled "Devices and Methods for Advancing a Wire," filed Jun. 29, 2018, hereby incorporated by reference in its entirety. However, manipulating two catheters while simultaneously trying to trying to visualize the positions of both catheters may be cumbersome for a user. Accordingly, various embodiments described herein are directed to reducing the number of catheters to a single catheter while providing visualization to allow a user to readily determine a location of a treatment portion of a catheter.

These and additional features will be discussed in greater detail below.

The vasculature of a potential subject (e.g., patient) may be tortuous. Additionally, each subject's vasculature may vary to provide each subject with uniquely positioned blood vessels (e.g., veins and arteries). Accordingly, in some embodiments, prior to a vascular treatment, systems as described may be used to scan a vasculature at an around a treatment portion of a subject to map the vasculature of the subject and/or determine a proper location for treatment (e.g., fistula formation). FIG. 1 illustrates a simplified depiction of the typical vascular anatomy an arm 10 around an elbow joint 12 including one or more blood vessels which may be targeted for vascular treatment. As shown, the brachial artery 20 extends superficially and distally from the upper arm and sinks deeply into the arm near the elbow joint 12, where the brachial artery 20 branches into the radial artery 22 and the ulnar artery 24. The upper portion of the ulnar artery 24 is deeply seated within the arm beneath the superficial flexor muscles (not shown), and leads down the ulnar side of the forearm to the wrist. Further down the arm, typically just below the radial tuberosity of the radius bone (not shown), the interosseous artery 26 branches off from the ulnar artery 24 and eventually feeds into the posterior and anterior interosseous arteries (not shown).

Also shown in FIG. 1 are the cephalic vein 40, including the upper cephalic vein 42, the median cephalic vein 44, and the lower cephalic vein 46, and the basilic vein 50, including the upper basilic vein 52, the medium basilic vein 54, and the lower basilic vein 56. The upper cephalic vein 42 runs along the outer border of the bicep muscle (not shown) and continues down into the forearm as lower cephalic vein 46. The median cephalic vein 44 joins the cephalic vein 40 near the elbow joint 12. The upper basilic vein 52 runs along the inner side of the bicep muscle (not shown) and continues into the forearm as the lower basilic vein 56. The lower basilic vein 56 of the lower arm is sometimes referred to as the common ulnar vein. The median basilic vein 54 (in some instances referred to as the median cubital vein) joins the upper basilic vein 52 and the low basilic vein 56. The median basilic vein 54 and the median cephalic vein 44 are formed at the branching of the median antebrachial vein 58. Near the branching of the median antebrachial vein 58 into the median basilic vein 54 and the medial cephalic vein 44, a perforating branch 30 connects these vessels with the deep veins of the arm through the antebrachial fascia (not shown).

As shown in FIG. 1, perforating branch 30 communicates with a first deep ulnar vein 23 and a second deep ulnar vein 24. These deep ulnar veins 23/24 may run substantially parallel on either side of the ulnar artery 22 between the brachial artery 14 and the interosseous artery 18, and may branch away from ulnar artery 24 distal to the interosseous artery 16. Between the brachial artery 20 and the interosseous artery 26, the deep ulnar veins 23/24 are typically located in close proximity to the ulnar artery 20, and usually less than 2 mm separate the ulnar artery 22 from the deep ulnar veins 23/24. Along the length of the deep ulnar veins 23/24, transverse branches (not shown) may occasionally connect to the deep ulnar veins 23/24. Also shown in FIG. 1 are first brachial vein 13 and second brachial vein 15. The brachial veins 13/15 generally run along the brachial artery 14, and the deep ulnar veins 23/24 feed into the brachial veins 13/15 near the elbow joint. Additionally, a pair of radial veins 17/19 may run along the radial artery 18, and may feed into one or both of the brachial veins 13/15.

In various embodiments, access to the ulnar artery and/or the ulnar vein may be achieved through an access site formed at the wrist or further up the arm into a superficial vein or artery. The catheter(s) may then be advanced through the vasculature to a treatment location. For example, it is often desirable to form a fistula between a vein and an artery proximate to a perforator (e.g., perforating branch 30) to increase blood flow from deep arteries to the superficial veins for such purposes as dialysis. Advancing a catheter from a superficial vein or artery makes accessing the site for fistula formation within the deep arterial/venous system easier.

It is noted that the vasculature within an arm is illustrated for example purposes only. It is contemplated that systems as described herein may be used to treat blood vessels anywhere within a body, human or animal (e.g., bovine, ovine, porcine, equine, etc.). For example, in some embodiments, blood vessels which are targeted and treated may include the femoral artery and femoral vein or the iliac artery and the iliac vein. In other embodiments, treatments between body conduits may not be limited to vein/artery treatments but may include treatment or fistula formation between adjacent veins, adjacent arteries or any other body conduits (e.g., bile ducts, esophagus, etc.).

Catheters

Generally, systems described herein are directed to endovascular treatment of a blood vessel. For example, systems described herein may be useful in measuring, modifying, and/or ablating tissue to form a fistula. The systems described here typically include one or more catheters. The one or more catheters may comprise one or more treatment portions. For fistula formation procedures, the one or more treatment portions may include one or more fistula-forming elements. The catheters described may further comprise elements to aid in visualization and/or alignment of one or more catheters as described in more detail herein. Any suitable catheter or catheters may be used with the systems described herein to form the fistulas other using the methods described herein The catheters may have any suitable diameter for intravascular use, such as, for example, about 4 French, about 5.7 French, about 6.1 French, about 7 French, about 8.3 French, between about 4 French and about 9 French, between about 4 French and about 7 French, between about 4 French and about 6 French, or the like.

Figure 2:
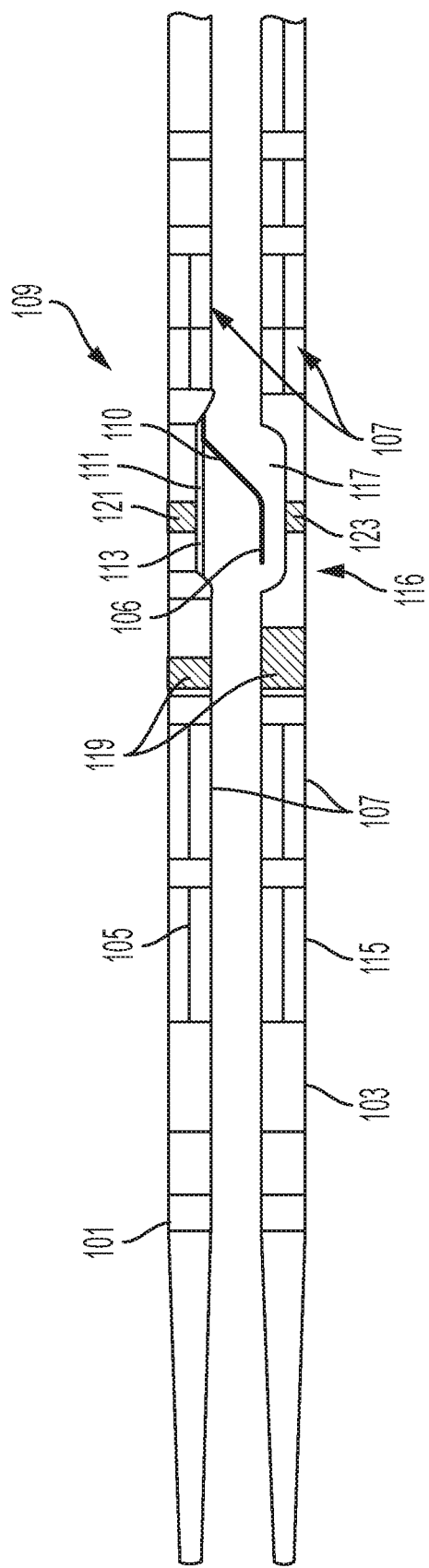
FIG. 2 depicts a two catheter system, according to one or more embodiments shown and described herein.
Figure 3:
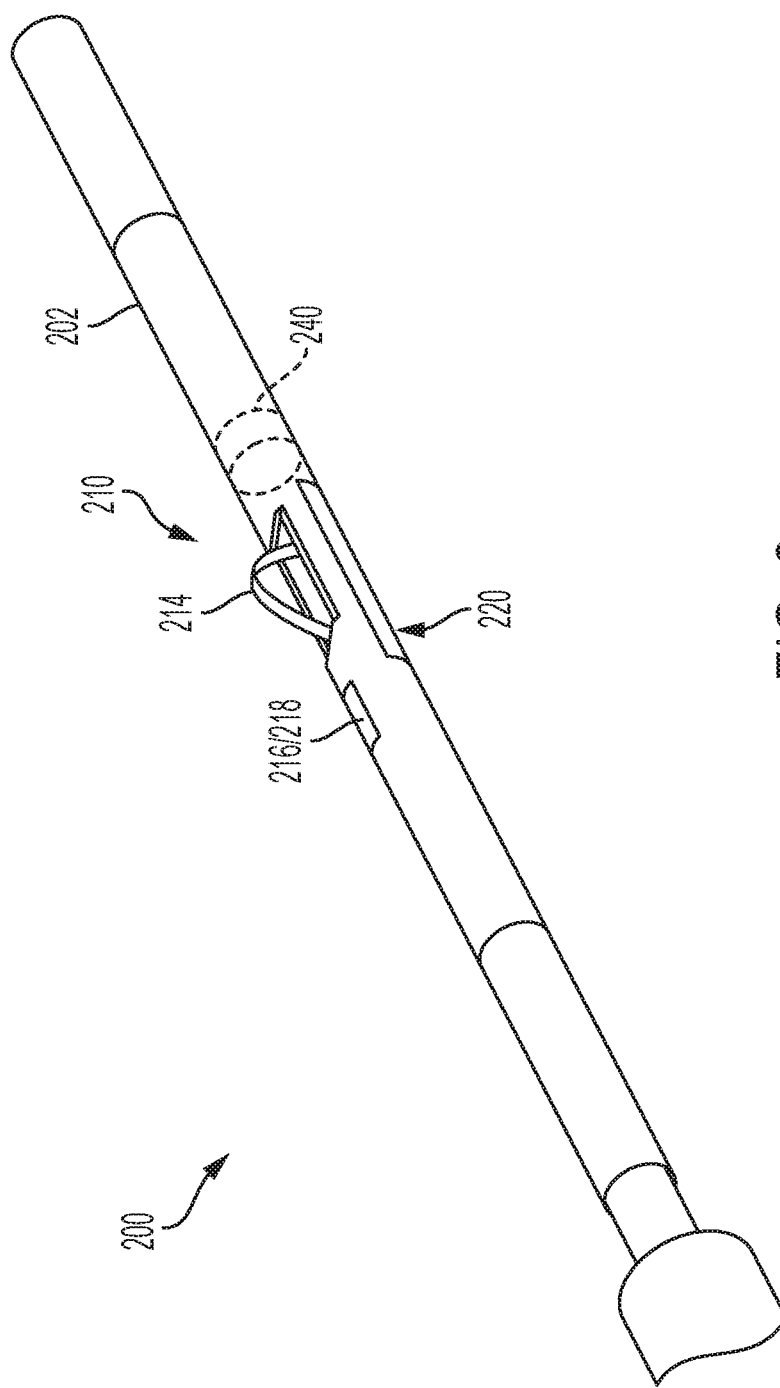
FIG. 3 depicts a single catheter system, according to one or more embodiments shown and described herein.

Referring now to FIGS. 2 and 3, various embodiments of one or more catheters are depicted. FIG. 2 generally illustrates one embodiment of a two catheter system while FIG. 3 illustrates an embodiment of a single catheter system. Accordingly, in embodiments incorporating a single catheter system, a second catheter is not necessary for supplying a desired treatment to a blood vessel. However, it is noted that various features of either the two catheter system or the single catheter system may be incorporated into either of the two systems. For example, an electrode such as illustrated in the single catheter system may be the same as an electrode used in the two catheter system.

As noted above, FIG. 2 generally illustrates one embodiment of a two catheter system configured to be used to form a fistula. As shown there, the system may include a first catheter 101 and a second catheter 103. The first catheter 101 may comprise a catheter body 105, one or more magnetic elements 107, and a treatment portion 109. As described herein, embodiments may be directed to fistula formation, accordingly the first catheter may include fistula-forming element 110 that may be used to form a fistula. In some variations, the fistula-forming element 110 may be advanced to project out of an opening 111 in the catheter body 105. The fistula-forming element 110 may comprise an electrode 106 configured to move between a low-profile configuration and an extended configuration in which it extends from the catheter body 105. In some variations the fistula-forming element may be spring-biased toward the extended configuration. That is, the electrode 106 may be configured to self-expand from the low-profile configuration to the extended configuration. Put yet another way, the electrode 106 may be in its natural resting state in the extended configuration. In some variations of electrodes moving between a low-profile configuration and an extended configuration, the electrode may be held in the low-profile configuration during placement of the catheter. For example, in some variations the electrode may be held in the low-profile configuration by the catheter body. The electrode may be released from the low-profile configuration when the electrode has been delivered to the location for fistula formation. For example, in some variations, the electrode may be released by moving the electrode in a proximal direction relative to the housing using a proximal control, as described in U.S. Pat. No. 9,017,323, entitled "Devices and Methods for Forming Fistula," filed Nov. 16, 2011, hereby incorporated by reference in its entirety. In other variations, the electrode may be held in a low-profile configuration by an external radially inward force on the electrode from a vessel wall during delivery, as described in U.S. Patent Application Publication No. 2017/0202616, entitled "Devices and Methods for Forming a Fistula," filed Jan. 15, 2017, hereby incorporated by reference in its entirety.

In some variations, the first catheter 101 may comprise a housing 113, which may help protect other components of the first catheter 101 during fistula formation. For example, when the fistula-forming element 110 comprises an electrode 106 configured to ablate tissue, the housing 113 may comprise one or more insulating materials which may shield or otherwise protect one or more components of the first catheter 101 from heat that may be generated by the electrode 106 during use.

As shown in FIG. 2, the second catheter 103 may also comprise a catheter body 115 and one or more magnetic elements 107. In variations where the first catheter 101 comprises a fistula-forming element 110 configured to project out the catheter body 105 of the first catheter 101, such as the variation depicted in FIG. 2, the catheter body 115 of the second catheter 103 may comprise a treatment portion 116 that includes a recess 117 therein, which may be configured to receive the fistula-forming element 110 as it passes through tissue. While shown in FIG. 2 as having a recess 117, it should also be appreciated that in some variations the treatment portion 116 of the second catheter 103 may not include a recess 117. In some variations, the treatment portion 116 of the second catheter 103 may include a fistula-forming element (not shown) in addition to or instead of the fistula-forming element 110 of the first catheter 101. Thus, in some variations, a fistula may be formed by one or more electrodes of one catheter, while in other variations, two catheters each comprising an electrode may simultaneously cut tissue from opposing sides to form a fistula.

In some variations, each of the one or more catheters may include one or more location indicators 119 configured to allow a control unit of the system to determine a location of the treatment portion of the catheter as it is advanced through the vascular of a subject (e.g., patient). For example, in one embodiment, each of the first catheter 101 and the second catheter 103 may include echogenic markers. The echogenic markers may be positioned proximate to the treatment portion of the catheter and may be visible to an imaging device such of an ultrasound imaging device. The echogenic markers may form particular patterns (e.g., a series of different sized echogenic rings with a specific spacing similar to a bar code) which may allow recognition of a particular catheter. Such pattern or ring may include marker bands made from, for example, platinum, iridium, or combinations thereof applied to the catheter proximate to the treatment portion of the catheter. In some embodiments, and as will be described in greater detail below, based on the echogenic markers a control unit, using a imaging device to capture image data of the one or more catheters, may be configured to determine a location of the treatment portion of the one or more catheters. In a two-catheter system such as illustrated in FIG. 2, each of the first and second catheters 101/103 may include echogenic markers which may be identical to or different from one another. Where the echogenic markers on each of the first and second catheters 101/103 vary from one another, a control unit may be able to determine which catheter is which. In some embodiments, echogenic markers may be used to indicate a rotational orientation of the one or more catheters. For example, a pattern of the echogenic marker when viewed under ultrasound may indicate in which direction the treatment portion of the particular catheter is facing.

In some embodiments, in addition to or in lieu of echogenic markers, the catheters 101/103 may include one or more location sensors 121/123, configured to output a signal indicative of a location of the catheter 101/103 (e.g., the treatment portion of the catheter). For example, the location sensor 121/123 may include an active electromagnetic sensor, a passive electromagnetic sensor, a permanent magnet, an RFID device, and or/an ultrasound transceiver. The location sensor 121 may be coupled to or positioned within the housing of the catheter at a position proximate to the treatment portion of the catheter. For example, a location sensor may be positioned longitudinally within the treatment portion 109/116 of the catheter 101/103. In some embodiments, a location sensor may be positioned proximal to and/or distal from the treatment portion 109/116 of the catheter 101/103. As will be described in greater detail below, a control unit may, based on the signal received from the location sensor 121, determine a location of the treatment portion 109/116 of the catheter 101/103 and follow a location of the catheter 101/103 in real time with an imaging device. It is noted that while the one or more location sensors 121/123 are illustrated as being in close proximity to the treatment portion 109/116, the one or more location sensors may be positioned anywhere along the housing of the catheter 101/103

It is noted that echogenic markers may be advantageous over electrically powered location sensors due to a need for tethering the location sensor to a power source. Accordingly, some echogenic markers may not require connection to a power source.

FIG. 3 illustrates an embodiment of a system including a single catheter 200. Catheter 200 may be substantially similar to catheter 101 described above. Similar to the first catheter 101 described in regards to FIG. 2 above, the catheter 200 may include a housing 202 and coupled to the housing 202 may be a treatment portion 210. In embodiments wherein endovascular treatment is directed to fistula formation, the treatment portion 210 may include an electrode 214 or other cutting device for forming a fistula. While the illustrated embodiment depicts an electrode 214 having an arc, the electrode 214 may be substantially similar to that described above and to the electrode described above in regards to the two catheter system. Additionally, and as noted above an electrode of the single catheter system may have features such as described in U.S. Pat. No. 9,017,323, entitled "Devices and Methods for Forming Fistula," filed Nov. 16, 2011, hereby incorporated by reference in its entirety, and U.S. Patent Application Publication No. 2017/0202616, entitled "Devices and Methods for Forming a Fistula," filed Jan. 15, 2017, hereby incorporated by reference in its entirety.

It is also contemplated that the catheter 200 may include one or more echogenic markers 216 and/or one or more location sensors 218, as described above in regard to FIG. 1. The one or more echogenic markers 216 and the one or more location sensors 218 may be positioned anywhere along the housing 202 of the catheter 200. For example, the one or more echogenic markers 216 may be positioned proximal to distal to, and/or within the treatment portion 210. Similarly, the one or more location sensors 218 may be positioned proximal to distal to, and/or within the treatment portion 210.

In addition, the catheter 200 may include one or more biasing mechanisms 220. A biasing mechanism 220 may be configured contact a wall of a blood vessel to bias the treatment portion 210 of the catheter 200 into contact with the wall (e.g., at a target treatment location) of the blood vessel. For example, the biasing mechanism 220 may be configured to expand to contact a first radial portion of a host blood vessel to bias the treatment portion 210 toward a second radial portion of the host blood vessel opposite the first radial portion. That is, the biasing mechanism 220 may expand to cause the catheter 200 to move laterally within the host blood vessel to cause the treatment portion 210 (e.g., cutting device, electrode, etc.) to contact a wall of the blood vessel. In some embodiments, the force of the biasing mechanism 220 may alter a shape of the blood vessel to extend the blood vessel in a direction opposite the movement of the biasing mechanism. Accordingly, the one or more biasing mechanisms 220 may be any mechanism configured to move the catheter transversely within a blood vessel to cause the treatment portion of the catheter to contact a treatment location within the blood vessel. Such biasing mechanism 220 may be positioned on opposite sides of the housing 202 from the treatment portion 210 of the catheter 200. Biasing mechanisms 220 may include, but are not limited to, balloons, cages, expandable wires, retracting mechanisms, etc. Various embodiments of biasing mechanisms will be discussed in greater detail with reference to FIGS. 4-13B.

In some embodiments, the catheter 200 may further include an intravascular imaging device 240 positioned within the housing 202 adjacent to the treatment portion 210. For example, the intravascular imaging device 240 may include IVUS, OCT, ICE, or the like. The intravascular imaging device 240 may be configured to provide a cross-sectional image at the position of the intravascular imaging device 240. As will be described in greater detail herein, the intravascular imaging device 240 may be used to determine a position of the catheter 200 within a blood vessel and/or the rotational alignment of the catheter 200, for example, the treatment portion 210 of the catheter 200. The intravascular imaging device 200 may be coupled to the housing 202 at a position distal to the treatment portion 210, proximal to the treatment portion 210, or longitudinally aligned with and/or within the treatment portion 210 of the catheter 200. In some embodiments, the one or more location sensors 220 may be incorporated in or positioned proximate to the intravascular imaging device 240. Various embodiments of the intravascular imaging device will be described in greater detail with reference to FIGS. 4-13B. It is noted that in some embodiments, there may not be an intravascular imaging device and instead an external imaging device (e.g., an external ultrasound probe) may be used.

Figure 4:
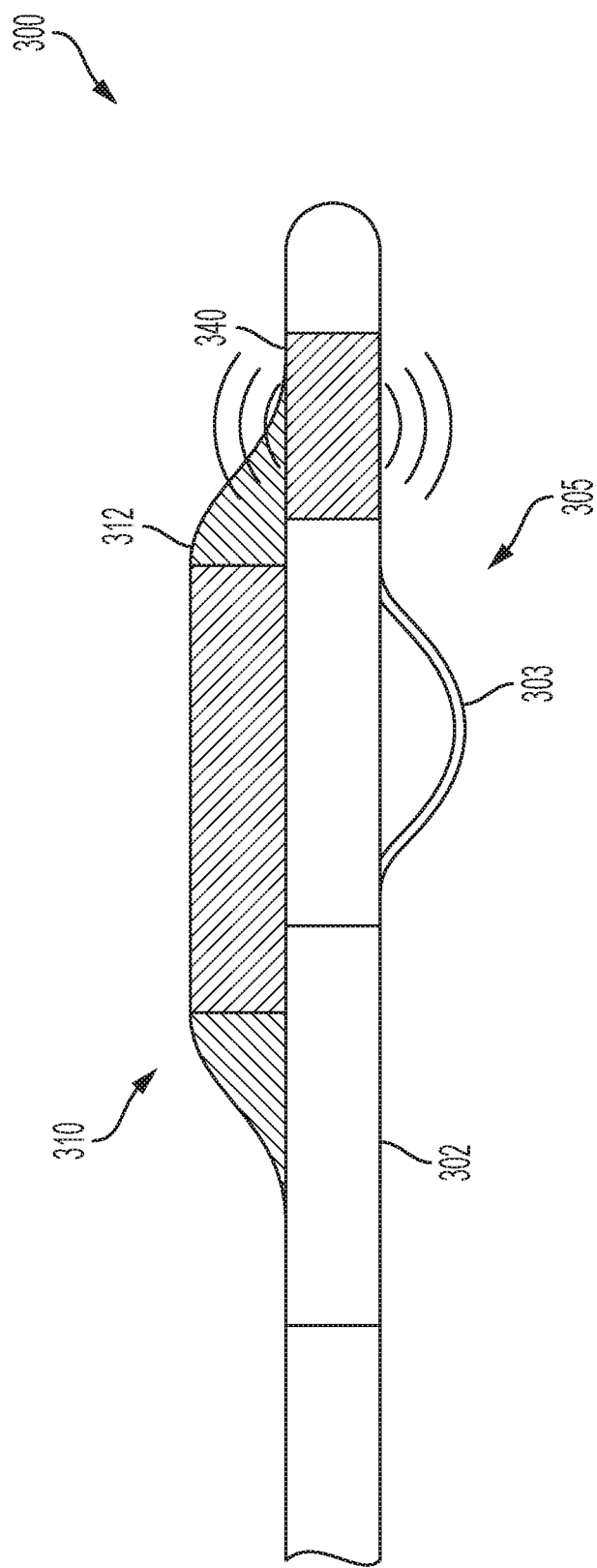
FIG. 4 depicts a cross-section of a single catheter system in an expanded state, according to one or more embodiments shown and described herein.

Referring now to FIG. 4, a cross section of an embodiment of a catheter 300 having a treatment portion 305 and a biasing mechanism 310 is depicted. In the depicted embodiment, the biasing mechanism 310 may be balloon that may be controllably expanded (e.g., controllably filled with saline). In the illustrated embodiment, the balloon is an asymmetrical balloon 312 that spans longitudinally across the treatment portion 302 of the catheter 300 on the opposite side of the housing 302. For example, in the present embodiment, the treatment portion 302 includes an electrode 303 and the asymmetrical balloon 312 is positioned directly opposite from the electrode 303. In the illustrated embodiment, the catheter 300 includes an intravascular imaging device 340 as described above, positioned distal (i.e., closer to the tip of the catheter) treatment portion. As will be described in greater detail herein, upon expansion of the biasing mechanism 310 the treatment portion 305 may be biased into contact with a treatment location of the blood vessel.

Figure 5A:
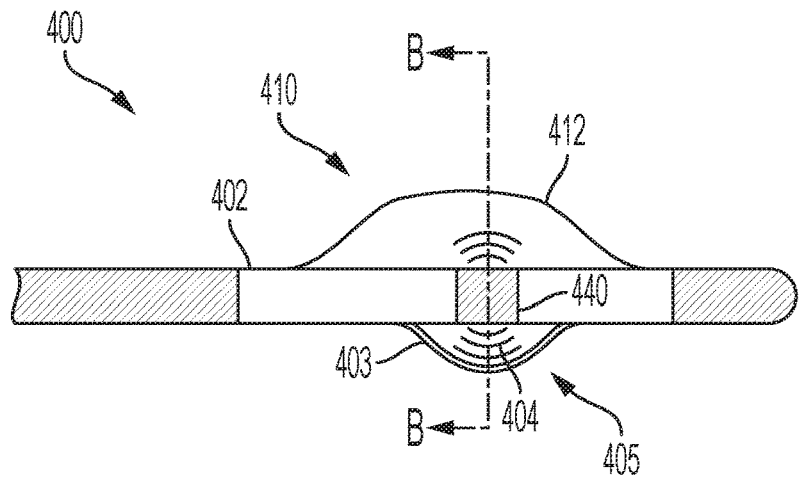
FIG. 5A depicts a cross-section of a single catheter system in an expanded state, according to one or more embodiments shown and described herein.
Figure 5B:
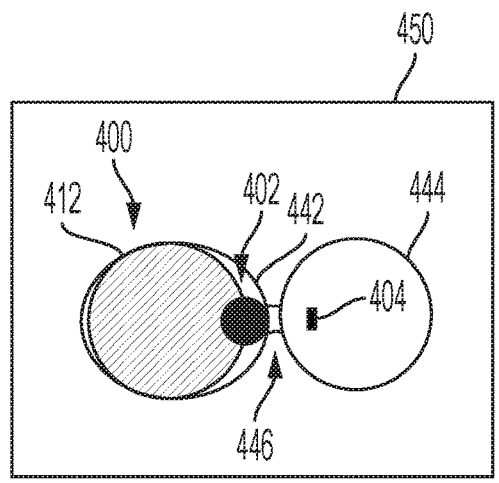
FIG. 5B depicts a axial cross-sectional view of the catheter of FIG. 5A deployed within a blood vessel, according to one or more embodiments shown and described herein.

FIGS. 5A and 5B illustrate a similar catheter 400 to that illustrated in FIG. 4. In the illustrated embodiment, the catheter 400 includes a treatment portion 405 and a biasing mechanism 410. As in FIG. 4, the biasing mechanism 410 may be an asymmetrical balloon 412 that spans across the treatment portion of the catheter on an opposite side of the housing 402. For example, in the present embodiment, the treatment portion 405 includes an electrode 403 having an arc that extends from the housing 402 and the asymmetrical balloon 412 is positioned directly opposite from the electrode 403. In the illustrated embodiment, the catheter 300 includes an intravascular imaging device 440 that is positioned within the housing 402 at a mid-point or apex 404 of the arc of the electrode 403. As noted above, the intravascular imaging device 440 may output image data depicting a cross-section of the catheter at the intravascular imaging device. For example, the cross-section may be aligned with the apex 404 of the electrode 403 as indicated by line B-B. FIG. 5B depicts an example image output on a display 450 of the intravascular imaging device 440 wherein the cross-section within a blood vessel 442 is taken at the apex 404 of the electrode 403. By taking the cross-section at the apex 404 of the electrode 404 it may be possible to determine a rotational alignment of the catheter based on the position of the apex 404 of the electrode as determined by the image data of the intravascular imaging device 440. Furthermore, because the intravascular imaging device 440 can continue transmitting during fistula formation with the electrode 403, it may be determined that the electrode has passed into a second blood vessel 444 from the first vessel 442 and that a fistula 446 has been created.

Figure 6:
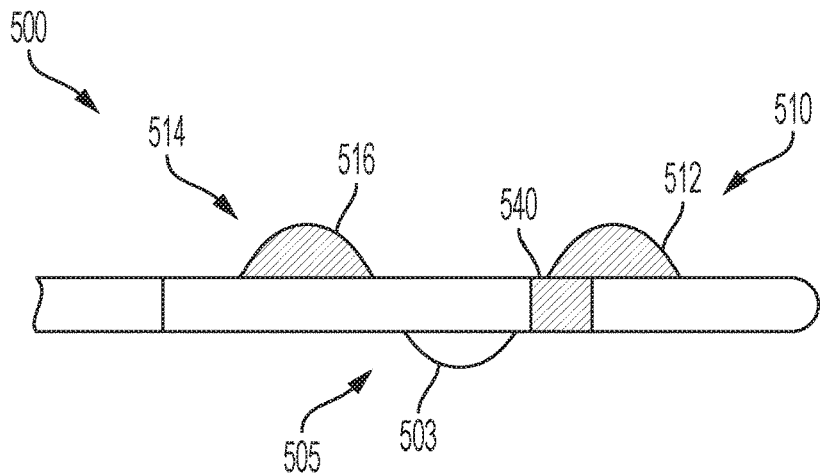
FIG. 6 depicts a cross-section of a single catheter system in an expanded state, according to one or more embodiments shown and described herein.

FIG. 6 illustrates another embodiment of a catheter 500 including a first biasing mechanism 510 and a second biasing mechanism 514. The first and second biasing mechanisms may be places proximal to and distal from the treatment portion 405. In such embodiment, the first and second biasing mechanisms may include balloons 512/516 (e.g., asymmetrical balloons). However, it is also contemplated that the first and second biasing mechanisms may be any biasing mechanism discussed herein. It is noted that by placing the balloons distal to and proximal to the treatment portion, it may be easier to isolate the electrode from fluid (e.g., saline) used to fill the balloons 512/516.

Furthermore, catheter 500 may include an intravascular imaging device 540. While the intravascular imaging device 540 is illustrated as being position distal to the treatment portion 505 (e.g., electrode 503), the intravascular imaging device 540 may be positioned anywhere along the catheter 500.

Figure 7:
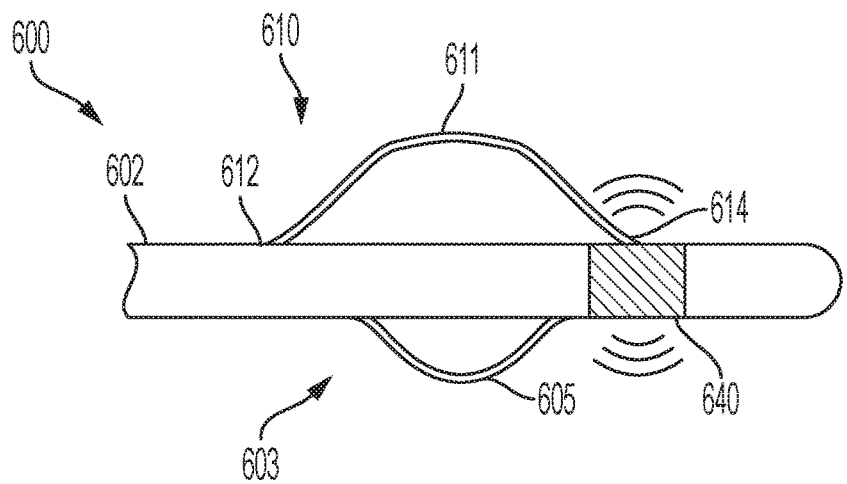
FIG. 7 depicts a cross-section of a single catheter system in an expanded state, according to one or more embodiments shown and described herein.
Figure 8A:
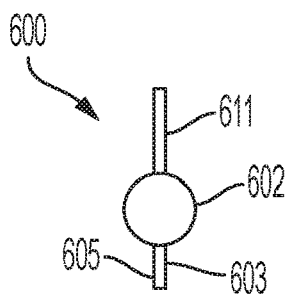
FIG. 8A depicts an axial cross-section of the catheter of FIG. 7 having a single biasing spring, according to one or more embodiments shown and described herein.
Figure 8B:
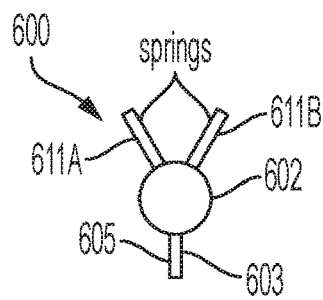
FIG. 8B depicts an axial cross-section of a catheter having two biasing springs, according to one or more embodiments shown and described herein.
Figure 8C:
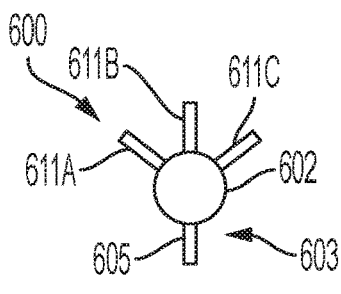
FIG. 8C depicts an axial cross-section of a catheter having three biasing springs, according to one or more embodiments shown and described herein.

FIG. 7 illustrates another embodiment of a catheter 600 including a treatment portion 603, an intravascular imaging device 640, and a biasing mechanism 610. In such embodiment, the biasing mechanism includes one or more expandable wires such as a biasing spring 611 (e.g., nitinol ribbon, wire, etc.) that is configured to bias the treatment portion 603 into contact with a blood vessel. The biasing spring 610 may be coupled to the housing 602 of the catheter at a first end 612 and a second end 614 proximal and distal to the treatment portion so as to span the treatment portion 603 on an opposite side of the housing 602 from the treatment portion 603. In some embodiments, the biasing mechanism 610 may include a single biasing spring 611 (FIG. 8A), two biasing springs 611A, 611B (FIG. 8B), or three biasing springs 611A, 611B, 611C (FIG. 8C). However, a greater number of biasing springs are contemplated and possible. The biasing springs may extend radially from the housing as illustrated in FIGS. 8A-8C.

As noted above, catheter 600 may include an intravascular imaging device 640. While the intravascular imaging device 640 is illustrated as being position distal to the treatment portion 603 (e.g., electrode 605), the intravascular imaging device 640 may be positioned anywhere along the catheter 600.

Figure 9:
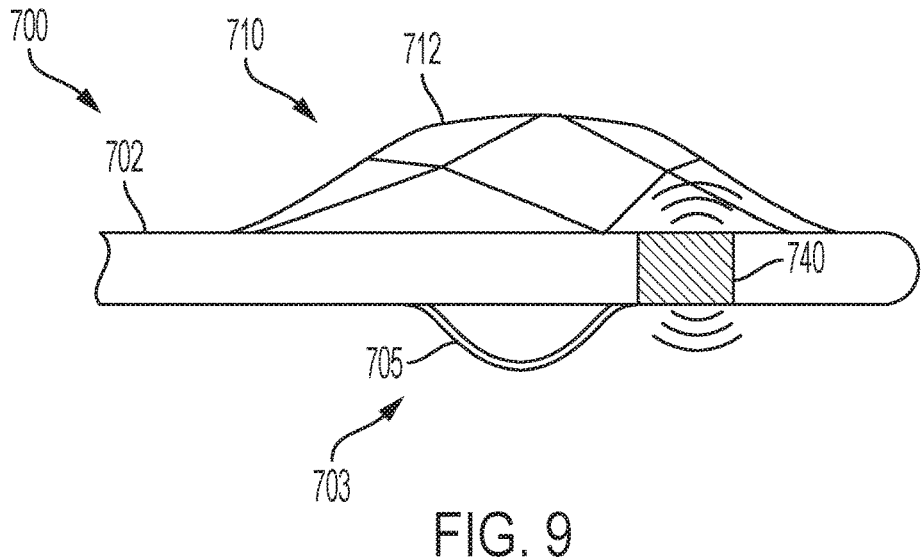
FIG. 9 depicts a cross-section of a single catheter system in an expanded state, according to one or more embodiments shown and described herein.

FIG. 9 illustrates another embodiment of a catheter 700 including a treatment portion 703, an intravascular imaging device 740, and a biasing mechanism 710. In such embodiment, the biasing mechanism 700 includes a self-expanding cage 712 (e.g., nitinol cage) coupled to the housing of the catheter 700 opposite the treatment portion 703 (e.g., electrode 705). The self-expanding cage 712 is configured to bias the treatment portion 703 into contact with a blood vessel. The self-expanding cage 712 may be coupled to the housing 702 of the catheter 700 opposite the treatment portion 703 so as to span the treatment portion 703.

As noted above, catheter 700 may include an intravascular imaging device 740. While the intravascular imaging device 740 is illustrated as being position distal to the treatment portion 703 (e.g., electrode 705), the intravascular imaging device 740 may be positioned anywhere along the catheter 700.

It is noted that each of the embodiments of the biasing mechanism may be positioned in an un-expanded position via a retractable sheath (not shown). In other embodiments, the biasing mechanism may be actuated by an operator.

FIGS. 10 and 10B illustrate an embodiment of a catheter 800 including a housing 801, a retractable sheath 804, and a biasing mechanism 806, and a treatment portion 808. The treatment portion 808 may include a spring biased electrode 810, such as described above. The retractable sheath 804 may hold the spring biased electrode 810 in a retracted position. The biasing mechanism 806 may be coupled to the housing 801 at a position proximate to the treatment portion 808. The biasing mechanism 806 may include one or more expandable wires moveable between a collapsed position and an expanded position, wherein at least a portion of the one or more expandable wires are spaced from an outer wall of the housing of the catheter 801. For example, in this embodiment, the biasing mechanism 806 is illustrated as a biasing spring 814 that is retractable to a position within the housing 801 and expandable to a position outside of the housing 801 to bias the treatment portion 808 of the catheter 800. The retractable sheath 804 is configured to hold the biasing mechanism 806 in a retracted position until deployment is desired. Accordingly, retracting of the sheath 804 may deploy both the spring biased electrode 810 and the biasing spring 814 simultaneously.

The catheter 800 may include an intravascular imaging device 840. While the intravascular imaging device 840 is illustrated as being position distal to the treatment portion 808 (e.g., electrode 810), the intravascular imaging device 840 may be positioned anywhere along the catheter 800.

FIGS. 11A and 11B illustrate an embodiment of a catheter 900 including a housing 901, a treatment portion 908, and a biasing mechanism 906. In such embodiment, the housing 901 defines one or more lumens 910 extending therethrough. A deflection wire 912 may extend through the housing 901 to couple to the housing 901 at a position distal the treatment portion 908. The housing 901 may further define an opening 909, such that the housing 901 may deflected around the deflection wire 912. Such deflection may allow the treatment portion 908 to be biased toward a treatment location within a blood vessel. In operation, the catheter 900 may be advanced to a treatment location, the housing 901 may then be pushed distally, while an operator restricts motion of the deflection wire (e.g., by holding a proximal end of the deflection wire 912). As illustrated in FIG. 11B, such motion causes the housing 901 including the treatment portion 908 (e.g., electrode 914) to deflect away from the deflection wire 912. In other embodiments, the operator may instead restrict motion of the housing 901 and pull on the deflection wire 912 to cause the housing 901 to deflect away from the deflection wire 912. In embodiments, the deflection wire 912 may have a greater stiffness than the housing 901.

The catheter 900 may include an intravascular imaging device 940. While the intravascular imaging device 940 is illustrated aligned within the treatment portion 908 and aligned with an apex of the electrode 914, the intravascular imaging device 940 may be positioned anywhere along the catheter 900.

FIGS. 12A and 12B illustrated an embodiment similar to that illustrated in FIGS. 11A and 11B. In particular, FIGS. 12A and 12B depict a catheter 1000 including a housing 1001, a treatment portion 1008, and a biasing mechanism 1006. In such embodiment, the housing 1001 defines one or more lumens 1010 extending therethrough. A deflection wire 1011 may extend through the housing 1001 to couple to the housing 1001 at a position distal the treatment portion 1008. The housing 1001 may further define an opening 1012, such that the housing 1001 through which the deflection wire 1011 moves in and out of to provide a biasing force to bias the treatment portion 1008 into contact with a treatment location of a blood vessel. Accordingly, the deflection wire 1011 has a retracted configuration (as illustrated in FIG. 12A) wherein the deflection wire 1001 is disposed within the housing and an extended configuration wherein the deflection wire 1011 is positioned outside of the housing (as illustrated in FIG. 12B).

In some embodiments, the deflection wire 1011 may comprise a shape memory material wherein in its natural state the deflection wire 1011 deflects out of the housing 1001. For example, the deflection wire 1011 may be a leaf spring. In such embodiments, a user may hold the deflection wire (e.g., with a sheath) in the retracted configuration and when the catheter has reach the desired position, release the deflection wire 1001. In other embodiments, a user may instead manually advance or retract the deflection wire 1011 (e.g., may pulling/pushing a proximal end of the deflection wire 1011), to cause the deflection wire 1011 to retract or extend.

The catheter 1000 may include an intravascular imaging device 1040. While the intravascular imaging device 1040 is illustrated aligned within the treatment portion 1008 and aligned with an apex of the electrode 1014, the intravascular imaging device 1040 may be positioned anywhere along the catheter 1000.

FIGS. 13A-13F illustrate an alternative embodiment of a catheter 1100. In such embodiment, the catheter 1100 includes a housing 1101, a treatment portion 1108, and a biasing mechanism 1106. The biasing mechanism 1106 may include any biasing mechanism such as, for example, an asymmetrical balloon, a cage, a wire(s), or any other deflection mechanism discussed herein. The catheter 1100 may further include an intravascular imaging device 1140.

Figure 13A:
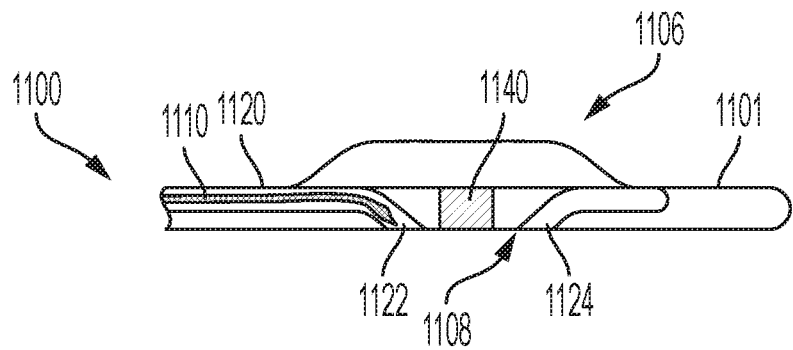
FIG. 13A depicts a cross-section of a single catheter system in an expanded state, according to one or more embodiments shown and described herein.
Figure 13B:
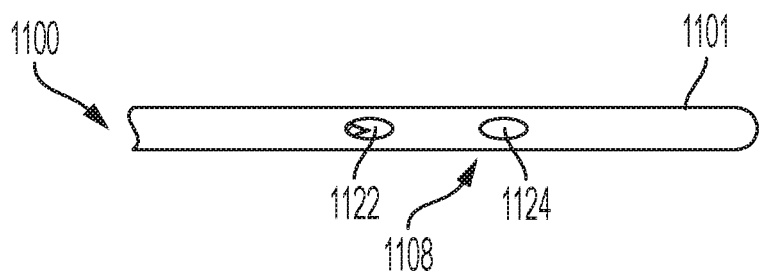
FIG. 13B depicts an exit point and a re-entry point of the catheter of FIG. 13A, according to one or more embodiments shown and described herein.

Referring to FIGS. 13A and 13B, the housing 1101 may define a lumen 1120 extending therethrough. The lumen 1120 may define an exit point 1122 and a re-entry point within the treatment portion 1108 of a catheter 1100. A cutting device 1110 (e.g., a nitinol needle) may be advanced through the lumen 1120 from a proximal position to a distal position, wherein the cutting device 1110 is extended through the exit point 1122 and through the re-entry point 1124. The cutting device 1110 may be produced from a shape memory material configured to bend as it exits the exit point 1122 to align itself for re-entry through the re-entry point 1124. The cutting device 1110 may be an electrode or other cutting device.

The biasing mechanism 1106 may be coupled to the housing 1101 opposite the exit and re-entry points 1122/1124. Accordingly, the biasing mechanism 1106 may bias the exit and re-entry point 1122/1124 into contact with a treatment location within a blood vessel.

In the present embodiment, the intravascular imaging device 1140 may be positioned longitudinally between the exit point and the re-entry point of the housing within the treatment portion 1108 of the catheter 1100. In other embodiments, the intravascular imaging device may be positioned longitudinally proximal or distal from the treatment portion 1108.

FIGS. 14A-14D illustrate a potential method for forming a fistula using catheter 1100 described in FIGS. 13A and 13B. In such embodiments, the catheter 1100 may be advanced within a first blood vessel 1180 (e.g., an artery or vein) to a position wherein the first blood vessel 1180 is positioned proximate to a second target vessel 1182 (e.g., a vein or artery). It is noted that while the catheter may be advanced through either the vein or artery, in some embodiments, it is beneficial to advance the catheter through an artery and form a fistula from the arterial side, as opposed to from the vein side, as going from a higher pressure artery to a lower pressure vein may provide for improved fistula formation. However, in other embodiments, the catheter may instead be advanced through a vein to a desired location. In yet further embodiments, a first catheter may be advanced through an artery and a second catheter may be advanced through a vein, such as in a two catheter system as discussed above.

Figure 14A:
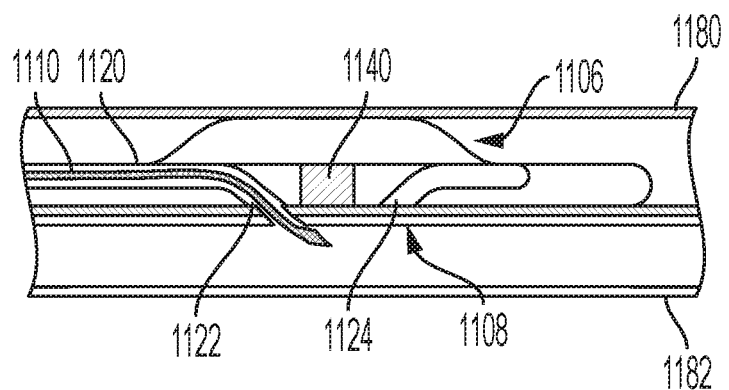
FIG. 14A depicts of a vessel with the catheter system of FIGS. 13A and 13B positioned therein, according to one or more embodiments shown and described herein.

Referring now to FIG. 14A, the catheter 1100 is advanced to a treatment location within the first blood vessel 1180. Based on imaging from, for example, the intravascular imaging device 1140, an operator may determine that the catheter 1100 is in the correct location for treatment (e.g., fistula formation between an artery and closely situated vein). Once in position, the biasing mechanism 1106 can be actuated to bias the treatment portion 1108 of the catheter into contact a treatment location (e.g., a desired portion of the vessel wall) of the first blood vessel 1180. In such cases, imaging using the intravascular imaging device 1140 may allow the operator to determine the treatment portion 1108 is rotationally aligned with the desired treatment location of the blood vessel. It is noted that in some embodiments, an intravascular imaging device 1140 may include a sensor (e.g., a location sensor) that outputs an indication of the rotational alignment of the intravascular imaging device 1140 which may correlate to or otherwise provide an indication of the rotational alignment of the treatment portion 1108 of the catheter 1100.

Figure 14B:
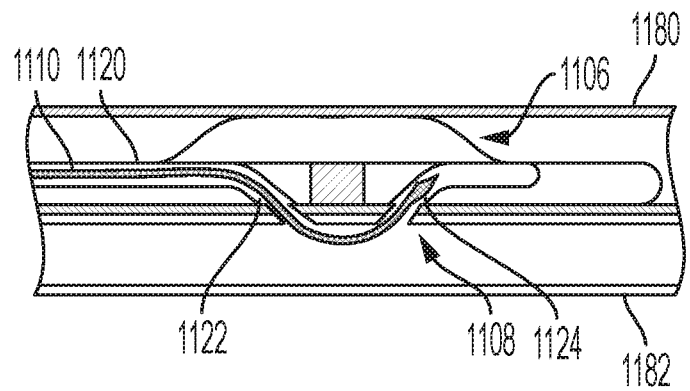
FIG. 14B depicts of the vessel of FIG. 14A with a cutting device being progressed from the first vessel into a second vessel and back into the first vessel, according to one or more embodiments shown and described herein.
Figure 14C:
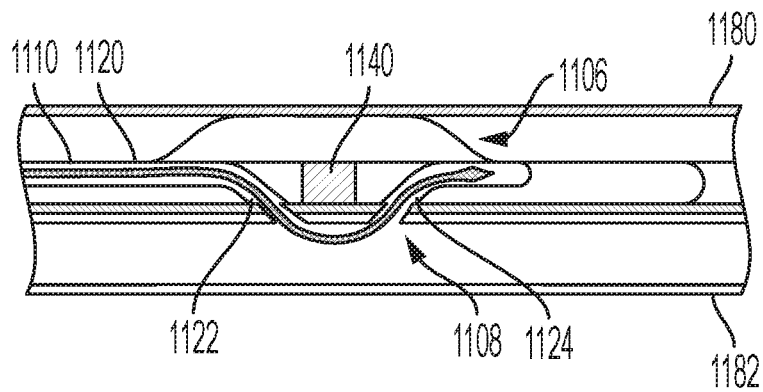
FIG. 14C depicts the cutting device of FIG. 14B being further advanced, according to one or more embodiments shown and described herein.
Figure 14D:
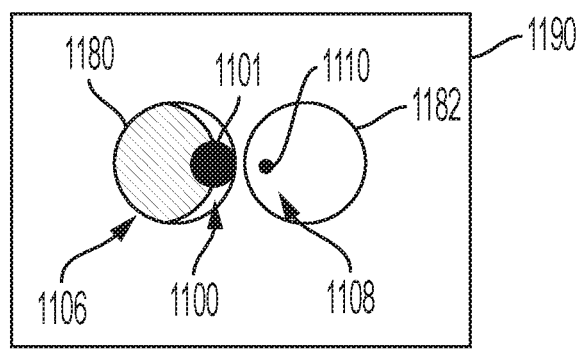
FIG. 14D depicts an axial cross-sectional view of the catheter, and first and second vessels of FIG. 14C, according to one or more embodiments shown and described herein.

Once in position, the cutting device 1110 may be advanced along the lumen through the exit point 1122 and into the second blood vessel 1182. In FIG. 14B, the cutting device 1110 may continue to be advanced such that the cutting device 1110 crosses back out of the second blood vessel 1182 and into the re-entry point 1124 of the catheter 1100. Referring to FIG. 14C, continuing to advance the cutting device 1110 may more closely sandwich the walls of the first and second blood vessels 1180/1182 between the cutting device 1110 and the housing 1101 of the catheter. FIG. 14D illustrate image data from the intravascular imaging device 1140, which may be displayed on a display 1190 communicatively coupled to the intravascular imaging device 1140. The image data may be an axial cross-section of the catheter 1100 and blood vessels 1180/1182 at the position of the intravascular imaging device 1140. Such cross-section illustrates the biasing mechanism biasing 1106 the treatment portion 1108 of the catheter 1100 toward contact with the treatment location of the blood vessel 1180. Additionally, the cutting device 1110 is illustrated as being positioned within the second blood vessel 1182. Accordingly, it can be confirmed that the cutting device has entered the second blood vessel. When in position, the cutting device 1110 may be activated (e.g., through RF energy) to create a fistula between the first blood vessel 1180 and the second blood vessel 1182. Using Doppler, fluoroscopy, or other imaging functions, it may be confirmed that a fistula has been created by monitoring blood flow between the two vessels through the fistula.

Systems and Methods

Various systems and methods will now be described including the various embodiments of the above-described catheters. It is noted that while only specific embodiments may be illustrated within the figures. The present system and methods may be applicable to any of the catheter systems described herein.

FIG. 15 generally schematically depicts communication between various modules within a system 1200 for endovascular treatment of a blood vessel. In particular, the system 1200 includes a communication path 1202, a control unit 1204, an imaging device 1206, and a display 1240. It is noted that in various embodiments a fewer or greater number of modules may be included within the system 1200 without departing from the scope of the present disclosure. Additionally, the system includes one or more catheters such as any of the two catheter or single catheter systems described herein above. That is the system may include a single catheter system configured to generate a fistula or deliver another type of vascular treatment to a target location within a vessel or a dual catheter system configured to generate a fistula between the two catheters or deliver some other type of vascular treatment.

The various modules of the system 1200 may be communicatively coupled to one another over the communication path 1202. The communication path 1202 may be formed from any medium that is capable of transmitting a signal such as, for example, conductive wires, conductive traces, optical waveguides, or the like. Moreover, the communication path 1202 may be formed from a combination of mediums capable of transmitting signals. In some embodiments, the communication path 1202 includes a combination of conductive traces, conductive wires, connectors, and buses that cooperate to permit the transmission of electrical data signals between the various components of the components such as processors, memories, sensors, input devices, output devices, and communication devices. Additionally, it is noted that the term "signal" means a waveform (e.g., electrical, optical, magnetic, mechanical or electromagnetic), such as DC, AC, sinusoidal-wave, triangular-wave, square-wave, vibration, and the like, capable of traveling through a medium.

The control unit 1204 can be any type of computing device and includes one or more processors and one or more memory modules. The one or more processors may include any device capable of executing machine-readable instructions stored on a non-transitory computer-readable medium, such as those stored on the one or more memory modules. Accordingly, each of the one or more processors may include a controller, an integrated circuit, a microchip, a computer, and/or any other computing device.

The one or more memory modules of the control unit 1204 are communicatively coupled to the one or more processors. The one or more memory modules may be configured as volatile and/or nonvolatile memory and, as such, may include random access memory (including SRAM, DRAM, and/or other types of RAM), flash memory, secure digital (SD) memory, registers, compact discs (CD), digital versatile discs (DVD), and/or other types of non-transitory computer-readable mediums. Depending on the particular embodiment, these non-transitory computer-readable mediums may reside within the control unit 1304, as shown, and/or external to the control unit 1304. The one or more memory modules may be configured to store logic (i.e., machine readable instructions) that, when executed by the one or more processors, allow the control unit to perform various functions that will be described in greater detail below.

The imaging device 1206 may be any imaging device configured to capture image data of the one or more catheters and surrounding vasculature as the catheter is advanced through the blood vessel. For example, and as described above, the imaging device 1306 may be an intravascular imaging device (e.g., IVUS, ICE, OCT, etc.) coupled to the housing of the catheter. Intravascular imaging devices are described in greater detail above. In other embodiments, the imaging device 1306 may be an external imaging device such as, for example an ultrasound device (e.g., a 2D ultrasound device and/or a 3D ultrasound device).

The imaging device 1206 may be communicatively coupled to the control unit over the communication path. Based on the data received from the imaging device 1306, the control unit may be able to process the image data to determine the rotational orientation of the catheter, and more specifically, the rotational orientation of the treatment portion of the catheter. In two catheter systems, the control unit may be able to determine proper alignment (e.g., longitudinal, rotational, and distance) between the two catheters for delivery of a vascular treatment.

As noted above, the system 1200 further includes a display 1240 communicatively coupled to the other modules of the system 1200 over the communication path 1202. The display 1240 may be any type of display configured to display image data from the imaging device 1206. In some embodiments, the control unit 1204 may process image data and with the display, project indicators onto the image to indicate, for example, rotational alignment, longitudinal alignment, distance between blood vessels, blood vessel labels (artery, catheter, perforator, etc.), etc. In embodiments wherein the imaging device comprises Doppler functionality, the control unit may be configured to display Doppler information include flow rate, volume, vessel pressure, etc. In various embodiments, the control unit may display the treatment portion of the catheter in real time as the treatment portion is advanced through the vasculature of the patient.

As discussed herein, methods may include selection of a blood vessel for access. As noted above, access to a vein or artery may be provided at the wrist or elsewhere. The catheter may be advanced through the blood vessel to a desired location, such as proximate to a perforator. For example, with reference to FIGS. 16A-16D, a depiction of a display 1240 showing axial cross-section image data from the imaging device 1206 is generally depicted. The imaging device 1206 may show the catheter C being advanced through an artery A, comitant veins V may be positioned on either side of the artery A. The catheter C may be advanced until a perforator P to one of the veins becomes visible on the display. The catheter C may continue to be advanced or retracted until the perforator is shown to meld into the vein V from which it extends. That may be the desired position for vascular treatment (e.g., fistula formation) as it is close to the origin of the perforator P.

Figure 16A:
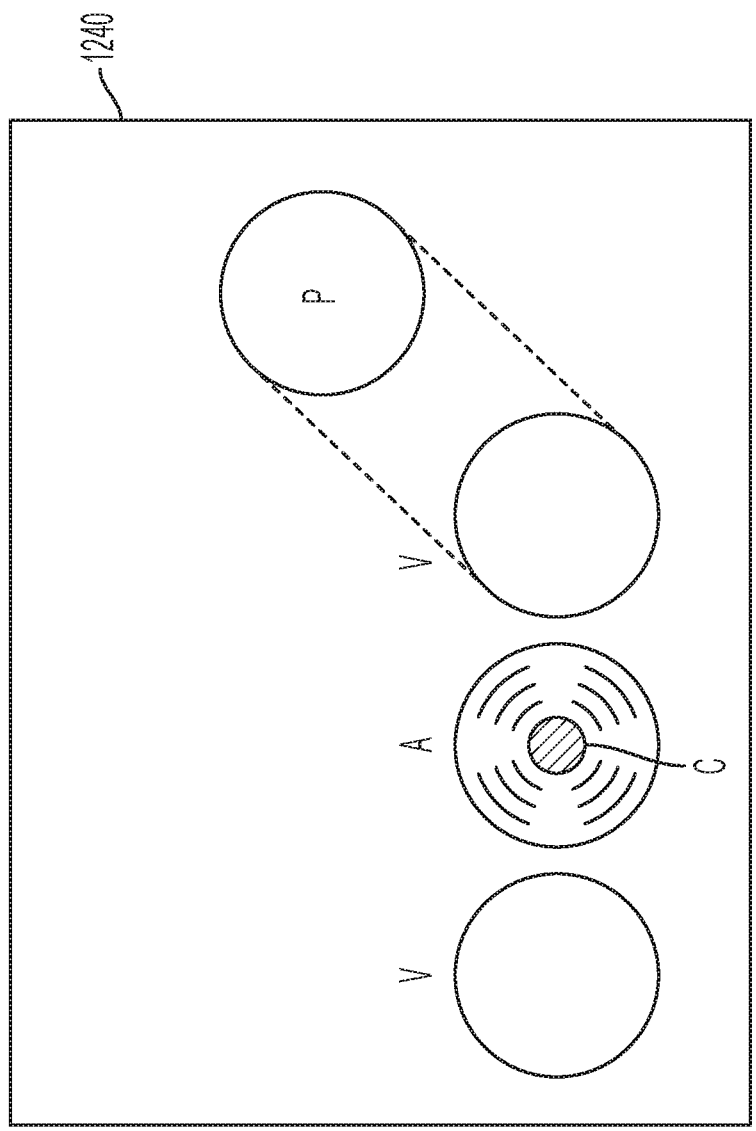
FIG. 16A depicts a display illustrating an endovascular treatment of a blood vessel, according to one or more embodiments shown and described herein.
Figure 16B:
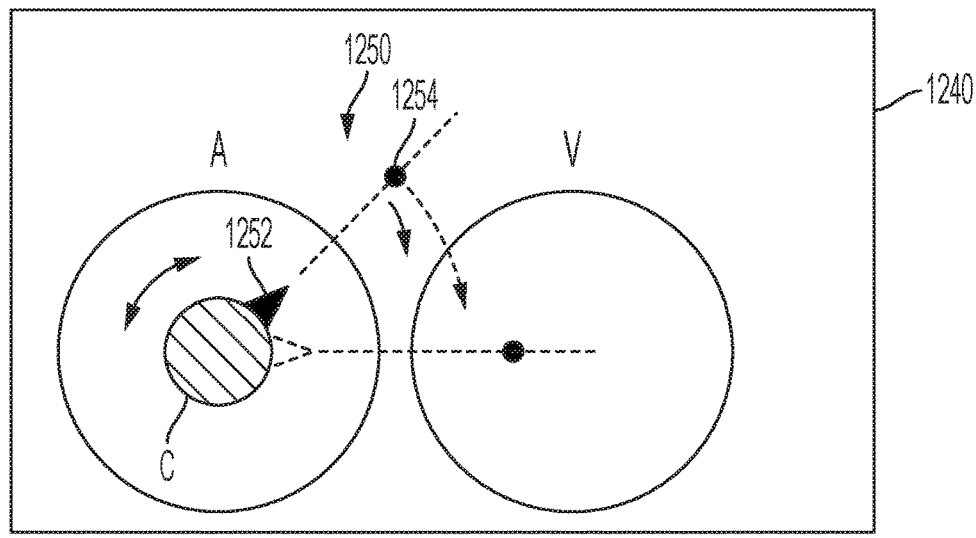
FIG. 16B depicts the display of FIG. 16A with an overlay, according to one or more embodiments shown and described herein.

As noted above, the control unit 1204 may be configured to determine a rotational positon of the catheter, and more specifically the treatment portion of the catheter. For example, and as noted above the catheter C may include one or more location sensors (e.g., including information from an intravascular imaging device as described herein) and/or echogenic markers that may be discernable by (e.g., through image recognition processing) or communicatively coupled to the control unit 1204. The one or more location sensors and/or echogenic markers may allow the system to follow and/or track the orientation and/or location of the treatment portion (e.g., the electrode) of the catheter C and produce an overlay such as illustrated in FIG. 16B to guide a physician or other user. In particular, FIG. 16B illustrates an overlay displaying an indicator 1250 which illustrates the rotational position of the treatment portion of the catheter C. For example, arrow 1252 illustrates the position and cutting direction of the treatment portion such that the position and cutting direction of the treatment portion is readily discernible on the display 1240. Additionally, the overlay may depict a cutting depth indicator 1254 which may provide an indication of the overall cutting depth of the treatment portion of the catheter C. FIG. 16B further illustrates rotation of the catheter to the desired orientation so as to be directed toward the treatment location within the blood vessel. During fistula formation, the treatment location may be the portion of the host blood vessel positioned closest to the target blood vessel.

Figure 16C:
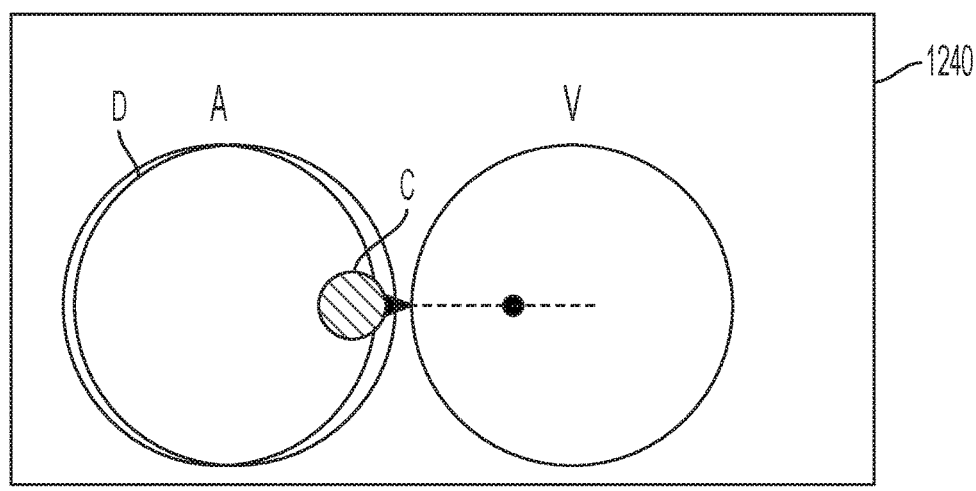
FIG. 16C depicts the display of FIG. 16A with a catheter deployed to provide an endovascular treatment, according to one or more embodiments shown and described herein.
Figure 16D:
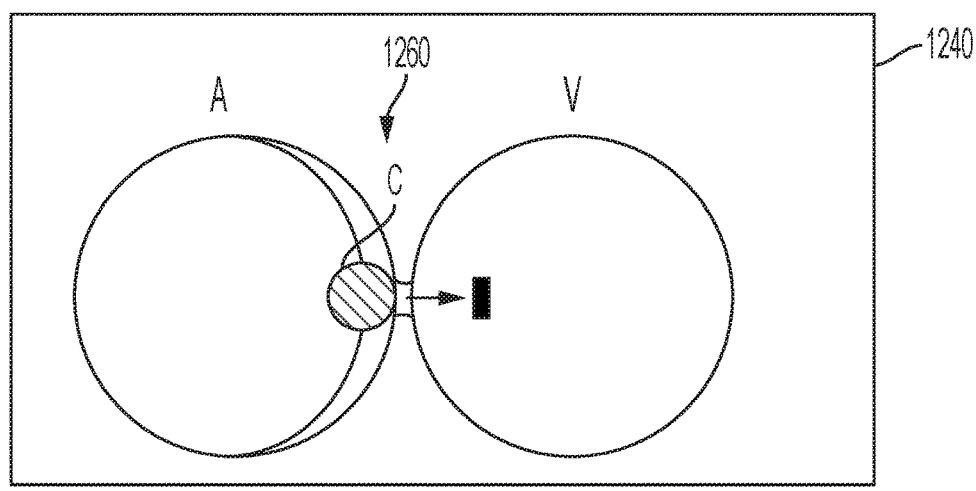
FIG. 16D depicts a fistula formation, according to one or more embodiments shown and described herein.

Once in the desired alignment as the operator may determine from the display and overlay projected on the display, the operator can deploy the biasing mechanism D, such as discussed above, to bias the treatment portion into contact with the treatment location of the blood vessel, as illustrated in FIG. 16C. At FIG. 16D, the operator may then apply the vascular treatment, in the illustrated embodiment, a fistula 1260 is formed. Doppler and/or fluoroscopy may then be used to confirm treatment success.

It is noted that while the above-provided example is directed to fistula formation using a single catheter, other treatments are contemplated and possible. Additionally, systems incorporating two catheters may similarly be used. In such cases, each catheter may include an intravascular imaging device and an overlay may provide rotational orientation of both of the catheters.

However, as noted herein, in various embodiments, the imaging device may not be an intravascular imaging device. In such embodiments, and as will be described in greater detail below, an actuator may be coupled to the imaging device and communicatively coupled to the control unit such that the control unit can control motion of the imaging device through the actuator. In such embodiments, the control unit will follow a position of the treatment portion of the catheter with the imaging device such that real-time imaging of the treatment portion of the catheter may be shown on the display without the need for direct operator control of the imaging device.

Figure 17:
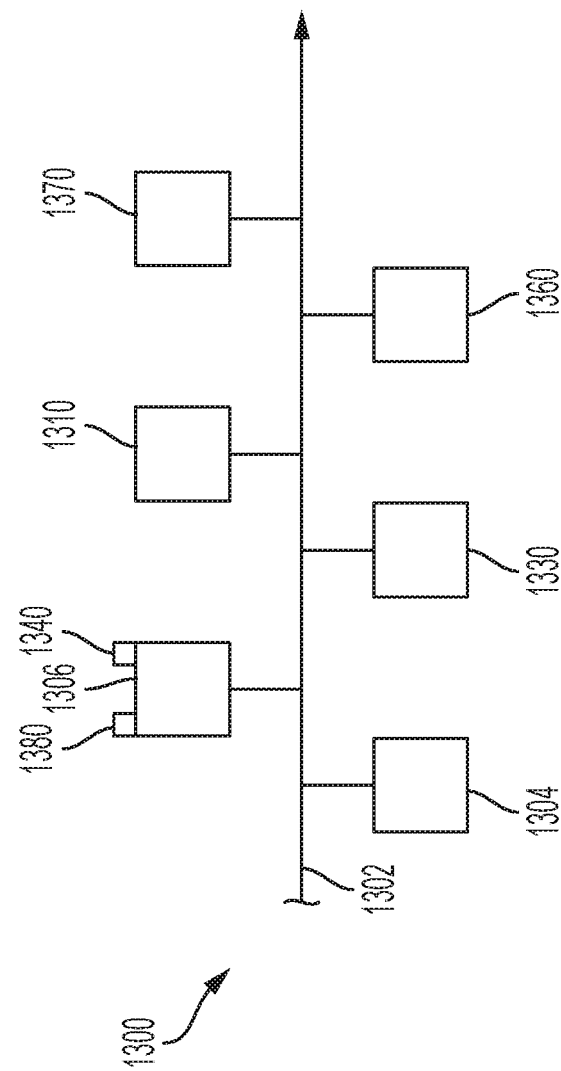
FIG. 17 schematically depicts communications between various modules of a system for endovascular treatment of a blood vessel, according to one or more embodiments shown and described herein.

FIG. 17 schematically illustrates an alternative embodiment of a system 1300 for endovascular treatment of a blood vessel. Similar to system 1200 described above, the system 1300 may include a communication path 1302, a control unit 1304, an imaging device 1306, and a display 1310. Unless as otherwise described below, the communication path 1302, the control unit 1304, and the display 1310 may be substantially identical to those described in relation to system 1200, above. In addition, the system 1300 may further include a user input device 1330, an actuator 1340, an electromagnetic field generator 1360, one or more location sensors 1380, and an energy source 1370. It is noted that in various embodiments a fewer or greater number of modules may be included within the system 1300 without departing from the scope of the present disclosure. Additionally, the system 1300 includes one or more catheters such as the catheters described herein above. That is, the system 1300 may include a single catheter system configured to generate a fistula or deliver another type of vascular treatment to a target location within a vessel or a dual catheter system configured to generate a fistula between the two catheters or deliver some other type of vascular treatment. Additionally, it is noted that while various modules are described in relation to system 1300, such modules may be incorporated within system 1200 described above, without departing from the scope of the present disclosure.

Figure 18:
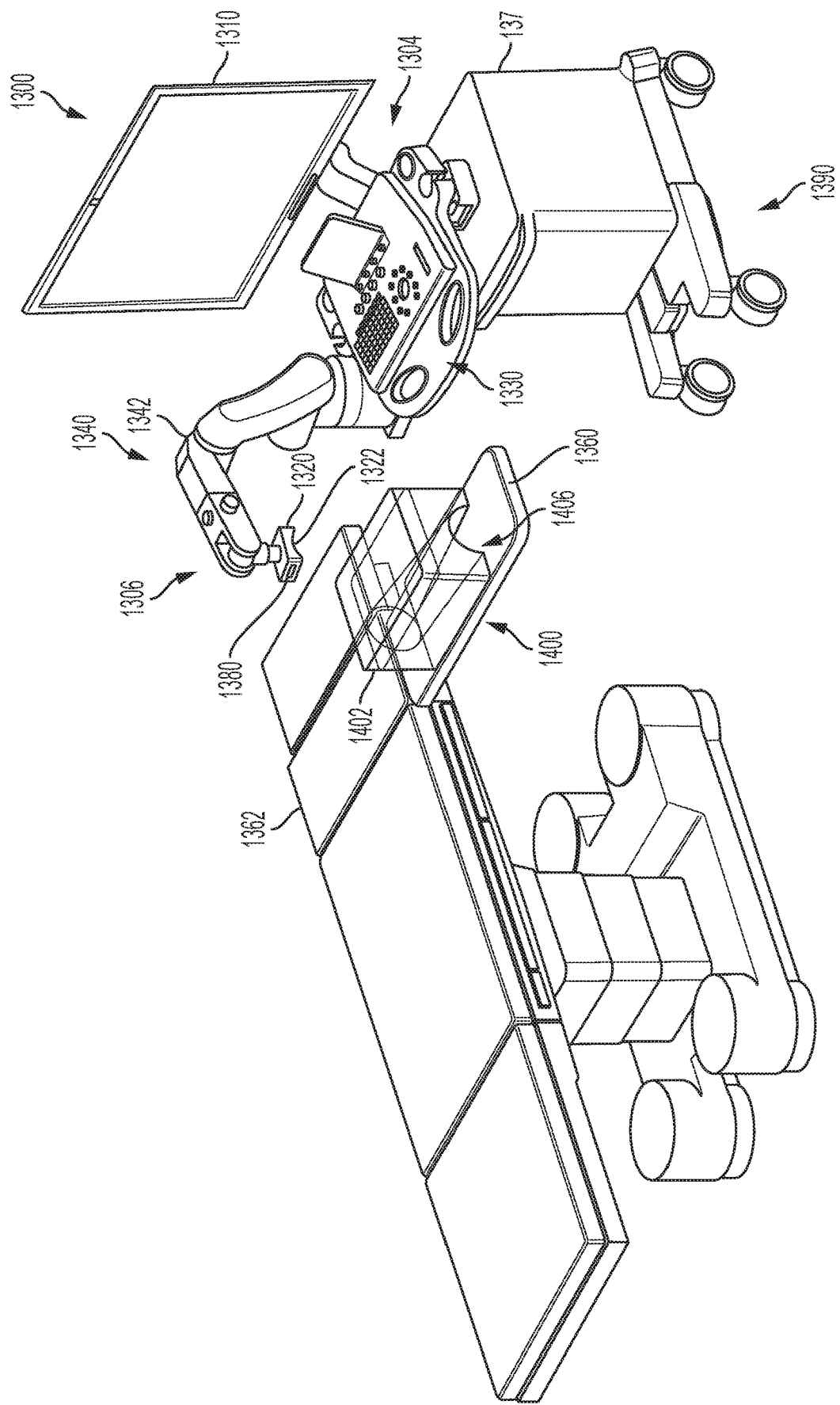
FIG. 18 depicts a perspective view of the system of FIG. 17, according to one or more embodiments shown and described herein.

FIG. 18 illustrates generally portions of the system 1300 for endovascular treatment of a blood vessel as may be provide within an exam room or doctor's office. As illustrated, various modules of the system may be mounted to a moveable cart 1390 that is able to be rolled from room to room. Accordingly, treatment locations for endovascular treatment may be improved since the system 1300 may be moved to a user. In other embodiments, there may not be a moveable cart. The moveable cart 1300 may support a variety of components of the system include, but not limited to, the control unit 1304, the imaging device 1306, the user input device 1304, the actuator 1340, etc.

Referring still to FIG. 18, as noted above, the system 1300 may include an imaging device 1306 communicatively coupled to the control unit 1304 over the communication path 1302. The imaging device 1306 may be an intravascular imaging device, as described above, or an external imaging device as illustrated in FIG. 18. The imaging device 1306, may be any device configured to provide images of a blood vessel of a subject. For example, in at least one embodiment, the imaging device is an ultrasound imaging device. In some embodiments, the imaging device is 2D ultrasound device or a 3D ultrasound device capable of capturing images of the desired blood vessel(s) along a frontal (coronal) plane, axial (transverse/cross-sectional) plane, and/or a sagittal plane.

The ultrasound device may capable of performing a variety of Doppler functions including, but not limited to, color Doppler, power Doppler, and Doppler vector flow. Using Doppler functions, the system 1300 may be able to analyze vascular flow to determiner arteries and veins. The system 1300 may illustrate these different vessels using different colored overlays, for example, on the display 1310 to allow an operator to quickly and efficiently determine which vessel is an artery and/or vein. Additionally, Doppler functionality may be used to ensure treatment success. For example, Doppler functionality may be able to determine successful fistula creation. For example, Doppler may be used to identify or confirm blood flow through the fistula formed between the two blood vessels. It is noted that other imaging devices/solutions may be used including, fluoroscopy.

Referring now to FIG. 18, the imaging device 1306 includes an ultrasound probe 1340. The ultrasound probe 1340 may be coupled to the moveable cart 1390 via the actuator 1340 (e.g., a robotic arm 1342). In other embodiments, the ultrasound probe 1340 may not be coupled to the moveable cart 1390.

Referring collectively to FIGS. 17 and 18, in some embodiments, the imaging device 1306 may include a catheter tracking sensor 1380 coupled to the ultrasound probe 1320. The control unit 1304 may receive a catheter tracking signal from the catheter tracking sensor 1380 and determine a location of a treatment portion of the catheter. As will be described in greater detail herein, in some embodiments the ultrasound probe 1320 may be coupled to an actuator 1340 configured to move the ultrasound probe 1380 with the treatment portion of the catheter to follow a location of the treatment portion of the catheter in real time (e.g., as the catheter is advanced through the blood vessel). In some embodiments, the control unit 1304 may be configured to perform image recognition on an ultrasound image to recognize a treatment portion of a catheter to determine the location of the treatment portion of the catheter relative to the imaging device 1306. For example, as described above, the one or more catheters may include echogenic markers that the control unit may be configured to recognize with the imaging device 1306. Based on recognizing the echogenic markers, the control unit 1304 may control motion of the imaging device 1406, through the actuator 134, to follow the location of the treatment portion of the catheter in real time as the catheter is advanced through the blood vessel. In addition, the control unit may adjust settings of the ultrasound probe 1320 to automatically focus on the treatment portion of the catheter and surrounding vasculature and display focused images on the display 1310. For example, based on the location of the echogenic markers, the control unit may automatically track a depth of the echogenic markers and adjust image quality settings.

In some embodiments, the catheter tracking sensor 1380 may interact with a location sensor incorporated into the one or more catheters. For example, the catheter tracking sensor 1380 may be able to detect a signal output by the location sensor incorporated into the catheter to follow the location of the treatment portion of the catheter. In some embodiments, the system 1300 may include an electromagnetic field generator board 1360 that will generate an electromagnet field to facilitate tracking between the catheter tracking sensor 1340 and the location sensor of the catheter. Such electromagnetic field generator board 1360 may be situated, for example, underneath a treatment portion of the user to generator an electromagnetic field around the treatment portion of the user. Referring to FIG. 18, the electromagnetic field generator board 1360 may be coupled to a subject support surface 1362. The control unit 1304, may be operable to control activation and deactivation of the electromagnetic field generator board 1360.

Figure 19A:
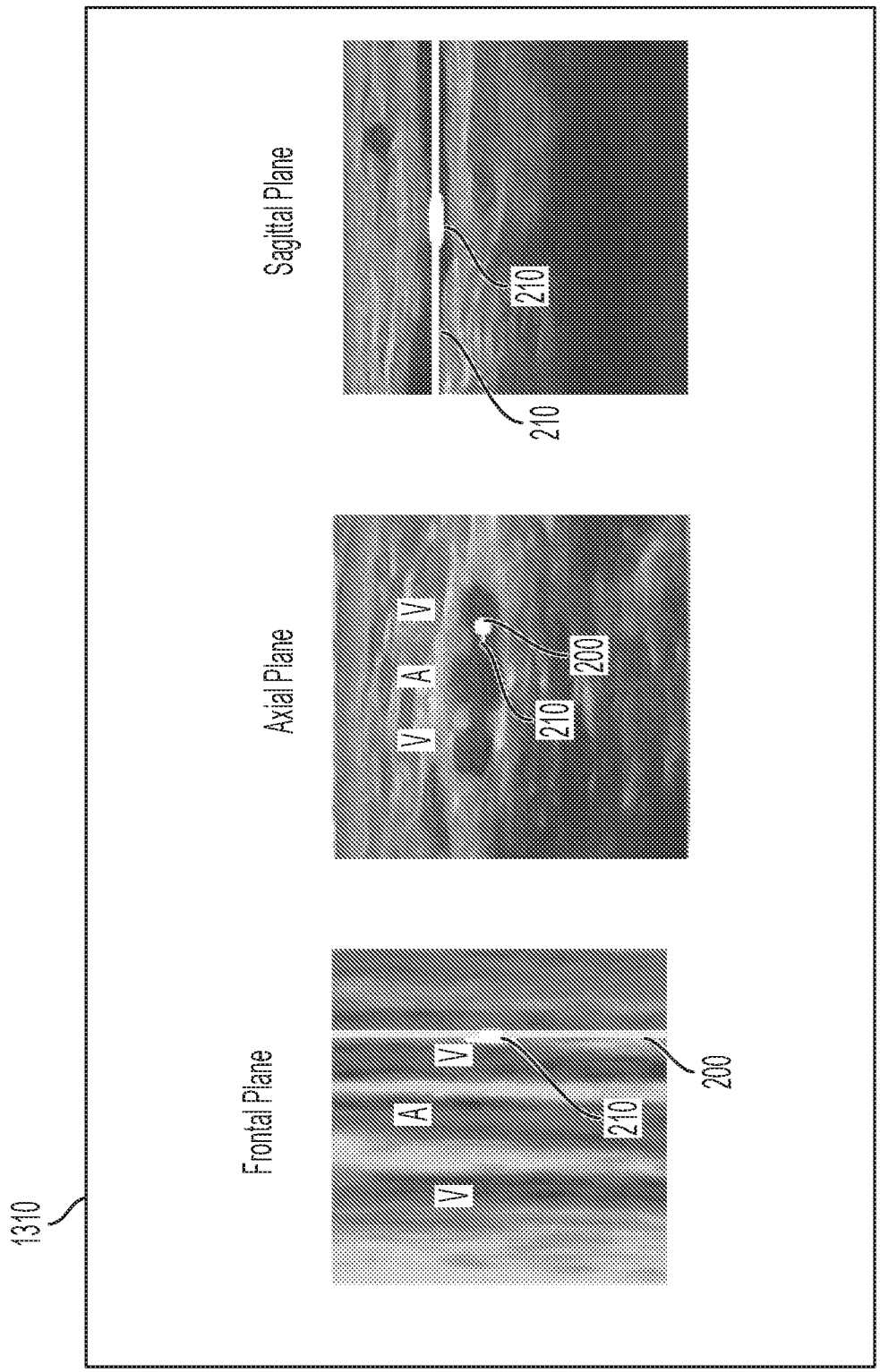
FIG. 19A depicts a display showing several views from an imaging device, according to one or more embodiments shown and described herein.
Figure 19B:
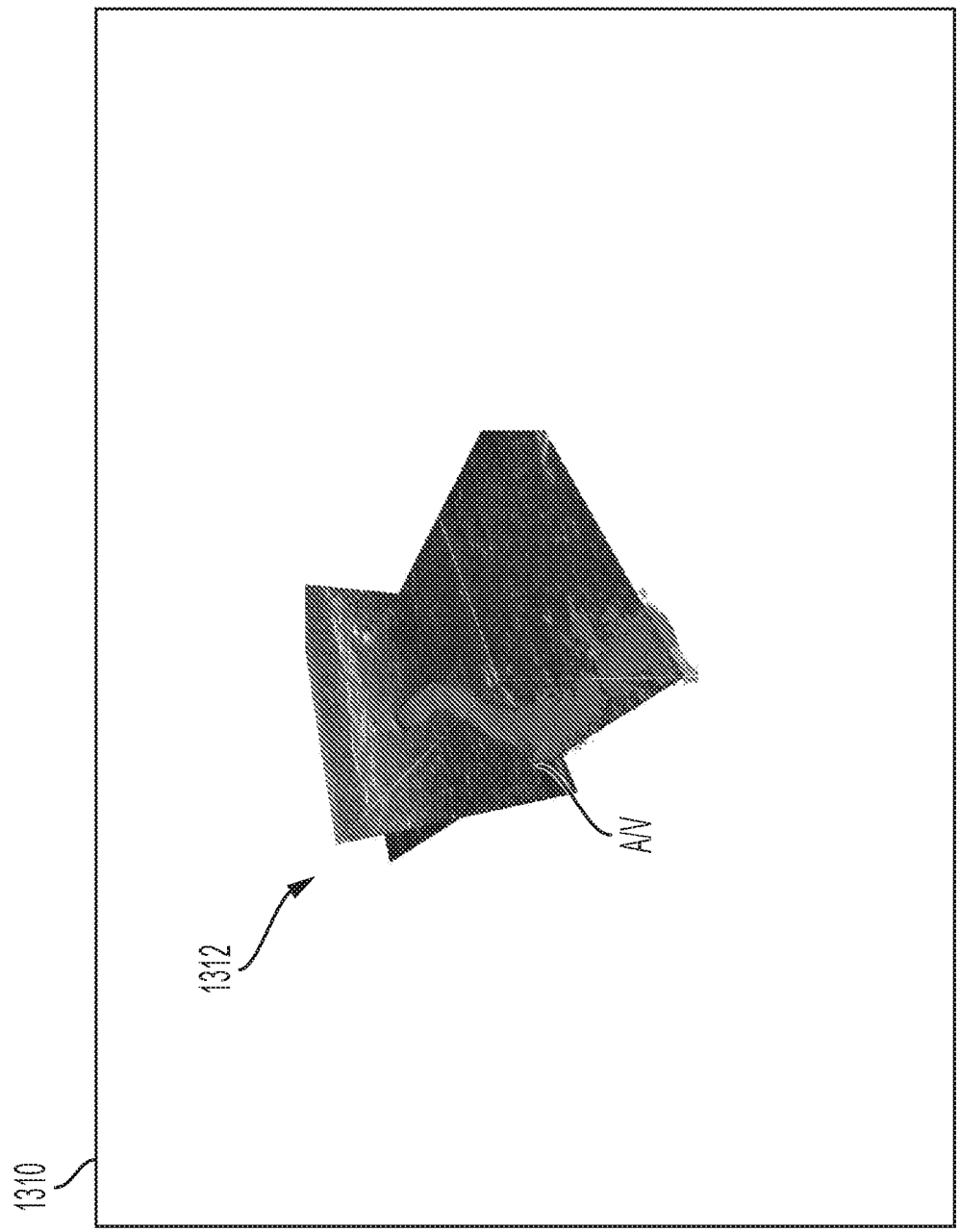
FIG. 19B depicts a display showing a 3-Dimensional Model of a vasculature of a subject, according to one or more embodiments shown and described herein.

As noted herein, based on the signals of the location sensor and/or the tracking sensor 1340, the control unit 1304 may determine a location of the treatment portion of the catheter and may be configured to automatically focus the settings of the imaging device to display various views of the treatment portion of the catheter including a sagittal view, an axial view, and/or a frontal view. For example, based on the signal of the location sensor, the control unit may automatically track a depth of the sensor and adjust image quality settings. Such views may cut through a center of the treatment portion of the catheter, such that each view shows a cross-sectional view of the catheter along in the sagittal plane, axial plane, and/or the frontal plane. FIG. 19A illustrates a display 1310 showing frontal plane view of a catheter 200 having a treatment portion being advanced through a vein V positioned proximate to an artery A in a frontal plane, axial plane, and a sagittal plane. In some embodiments, the control unit 200 will cause all three view to be display simultaneously. In other embodiments, the control unit 200 may only display two or fewer views. As noted herein, the control unit may 200 be configured to recognize various portions of the vasculature and provide an overly identifying the vasculature. Such overlay may include labels, colors, etc. For example, the overlay may provide a blue overlay to arteries to indicate arterial flow and a blue overlay to veins to indicate venous flow. In some embodiments, the control unit may be configured to generate a 3-Dimensional model of the vasculature of the subject. Referring to FIG. 19B an example 3-Dimensional model 1312 of a portion of the vasculature of the subject. For example, where a catheter having a location sensor and/or echogenic marker is tracked through an artery or vein using an imaging device (e.g., 2D or 3D ultrasound device), the control unit 200 may generate a 3-Dimensional model 1312 of the artery or vein A/V and display the same on the display 1310. Surrounding veins and arteries may also be identified and generated as part of the 3-Dimensional map. Arteries and veins may appear as different colors (e.g., red or blue), or otherwise labeled, to allow an operator to distinguish between the two.

Figure 20:
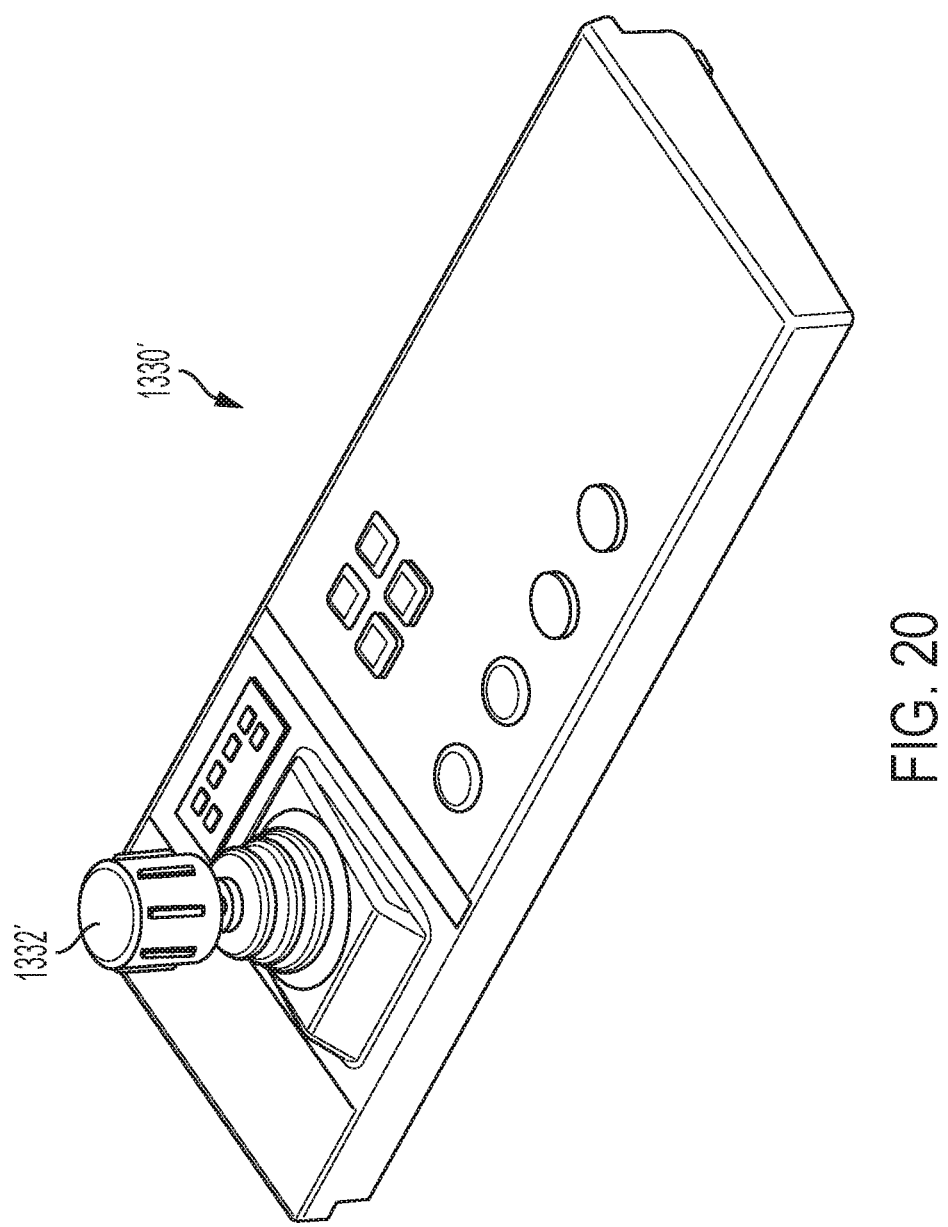
FIG. 20 illustrates a user input device, according to one or more embodiments shown and described herein.

Referring again to FIGS. 17 and 18, the system 1300 may further include one or more user input devices 1330 communicatively coupled to the control unit 1304. The one or more user input devices 1330 may include any device capable of transforming mechanical, optical, audible, or electrical signals into a data signal capable of being transmitted with the communication path 1302. Specifically, a user input device 1330 may include any number of movable objects that transform physical motion into a data signal that can be transmitted over the communication path 1302 such as, for example, joystick, a button, a keyboard, a switch, a knob, a microphone, or the like. FIG. 18 illustrates the user input device 1330 mounted to the moveable cart. Accordingly, an operator may input commands to the control unit 1304 through the user input device 1330. Such commands may include but are not limited, manual control of the imaging device, selecting particular views, or particular overlays. Referring to FIG. 20, an alternative user input device 1330 is generally depicted. Such user input device 1330' is illustrated as including a joystick 1332'. Based on a user input from the one or more user input devices 1330', the control unit may be configured to switch to a manual operation mode from an automatic following mode to allow for manual control of the ultrasound probe 1380 based on input from the one or more user input devices 1330'.

As noted above, the system 1300 may further include an actuator 1340 communicatively coupled to the control unit 1304 and physically coupled to the imaging device 1306 (e.g., ultrasound probe 1320). As noted herein, the control unit 1304 may be configured to move the imaging device 1306 with the actuator 1340. FIG. 18, illustrates an embodiment, wherein the imaging device 1340 includes an ultrasound probe 1320 (e.g., 3D ultrasound probe and/or a 2D ultrasound probe.) The actuator 1340 may include a robotic arm 1342 coupled to the ultrasound probe 1340. The robotic arm 1342 may be capable of 6 (or more) degrees of freedom of motion to control motion of the ultrasound probe 1320. The robotic arm 1342 may be coupled to the moveable cart 1390 so as to be moveable with the moveable cart 1390.

Figure 21:
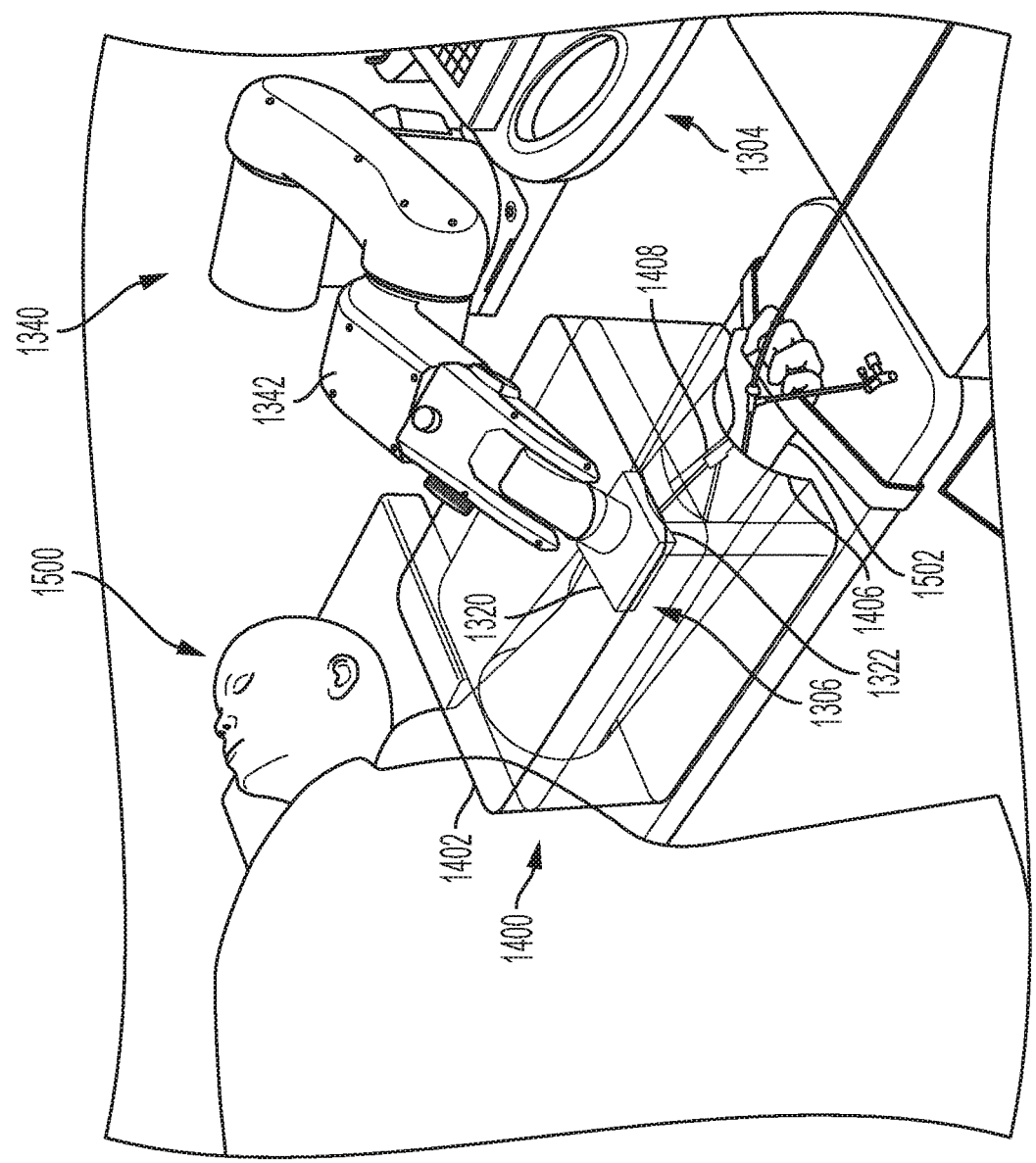
FIG. 21 illustrates an endovascular treatment being performed on a subject, according to one or more embodiments shown and described herein.

When using an external ultrasound imaging device, the ultrasound probe 1320 may include a subject contact surface 1322. The subject contact surface 1322 may be contacted to a treatment zone (e.g., arm, leg, torso, etc.) of a subject through a flexible subject interface/fluid barrier. That is, the subject contact surface 1322 may directly contact a treatment zone (e.g., arm, leg, etc.) of a patient or may directly contact the flexible fluid barrier 1408, which is directly contacted with the treatment zone of the subject. Such fluid barrier may be provided s part of a media bath 1400 configured to be placed over the treatment zone of a subject. For example, the media bath 1400, such as illustrated in FIG. 18, may include a fluid housing 1402 configured to hold fluid around the treatment zone of a subject. The fluid housing 1402 may include a shaped opening 1406 through which a treatment zone (e.g., arm, leg, etc.) of a subject may be disposed. For example, FIG. 21 illustrates a subject 1500 having an arm 1502 disposed within the shaped opening 1406. A flexible fluid barrier 1408 (e.g., plastic) may be situated between the subject 1500 and the fluid placed within the fluid housing 1402 and conform to the shape of the treatment zone of the subject 1500.

Once the subject 1500 is positioned, the robotic arm 1342 may be controlled either manually or automatically based on logic executed by the control unit 1304, to place the ultrasound probe within the media bath 1400 and in contact the subject contact surface 1322 with the subject 1500. In various embodiments, the system 1300 may be used without catheters to first map a vasculature of the subject to seek a desired location for vascular treatment (e.g., fistula formation). As noted herein, the system 1300 may be placed in an automatic catheter following mode, wherein the control unit 1304 automatically controls the robotic arm 1342 to cause the ultrasound probe 1306 to follow a position of a treatment portion of the catheter as it is advanced through the vasculature of subject to a target treatment location.

Figure 22:
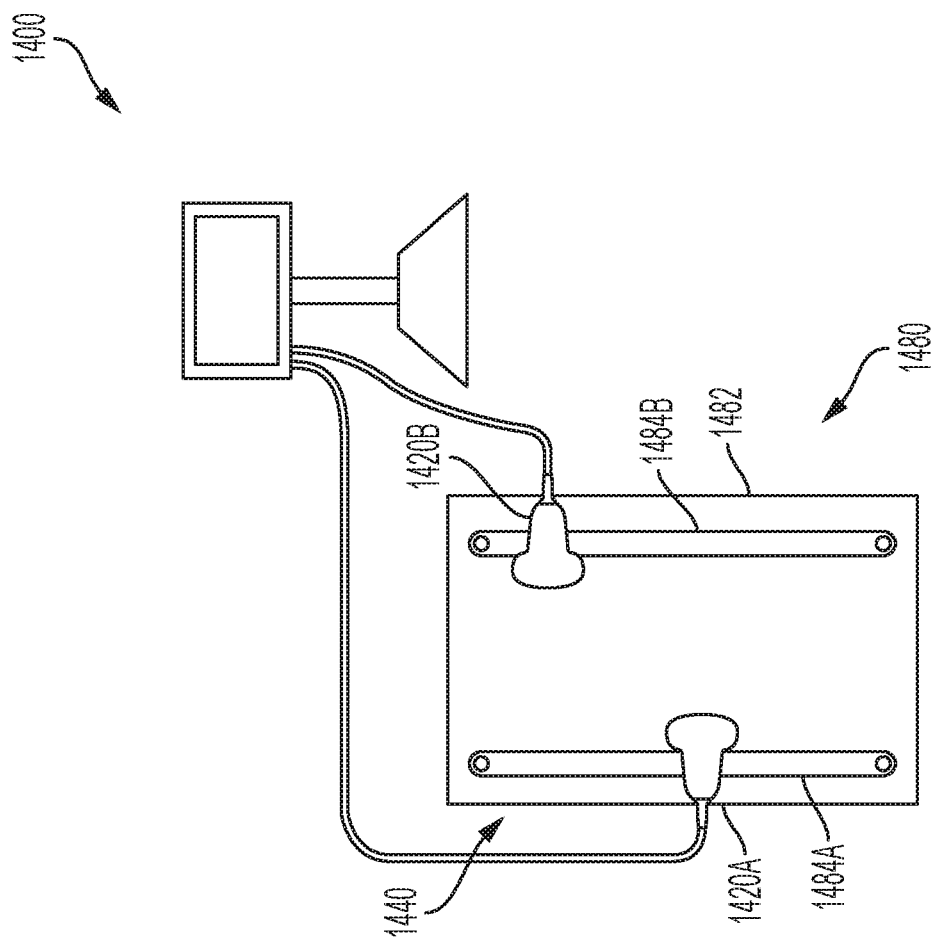
FIG. 22 illustrates a media bath and imaging device, according to one or more embodiments shown and described herein.

FIG. 22 illustrates an alternative embodiment of a system 1400, wherein an actuator 1440, and the imaging device 1306 is incorporated into a fluid housing 1482 of a media bath 1480. In such embodiments, the fluid housing 1482 may be provided with tracks 1484A/1484B along which one or more ultrasound probes 1420A/1420B (e.g., 2 probes) can track back and forth. In such embodiment, the actuator 1440 may include one or more linear actuators that interact with the one or more ultrasound probes 1420A/1420B to cause the one or more ultrasound probes to move 1420A/1420B along the tracks 1484A/1484B. In some cases, such as embodiments wherein two catheters are separately placed within blood vessels within the subject, each probe may be separately controlled to separately track each catheter and to provide image data of the treatment portion of each catheter.

Figure 23B:
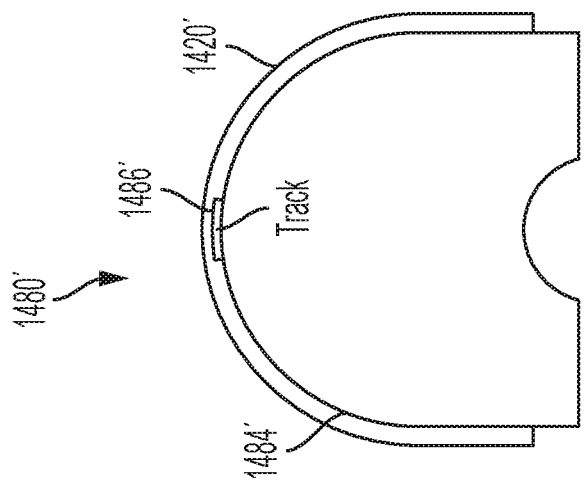
FIG. 23B illustrates a front view of the media bath and imaging device of FIG. 23A, according to one or more embodiments shown and described herein.
Figure 23A:
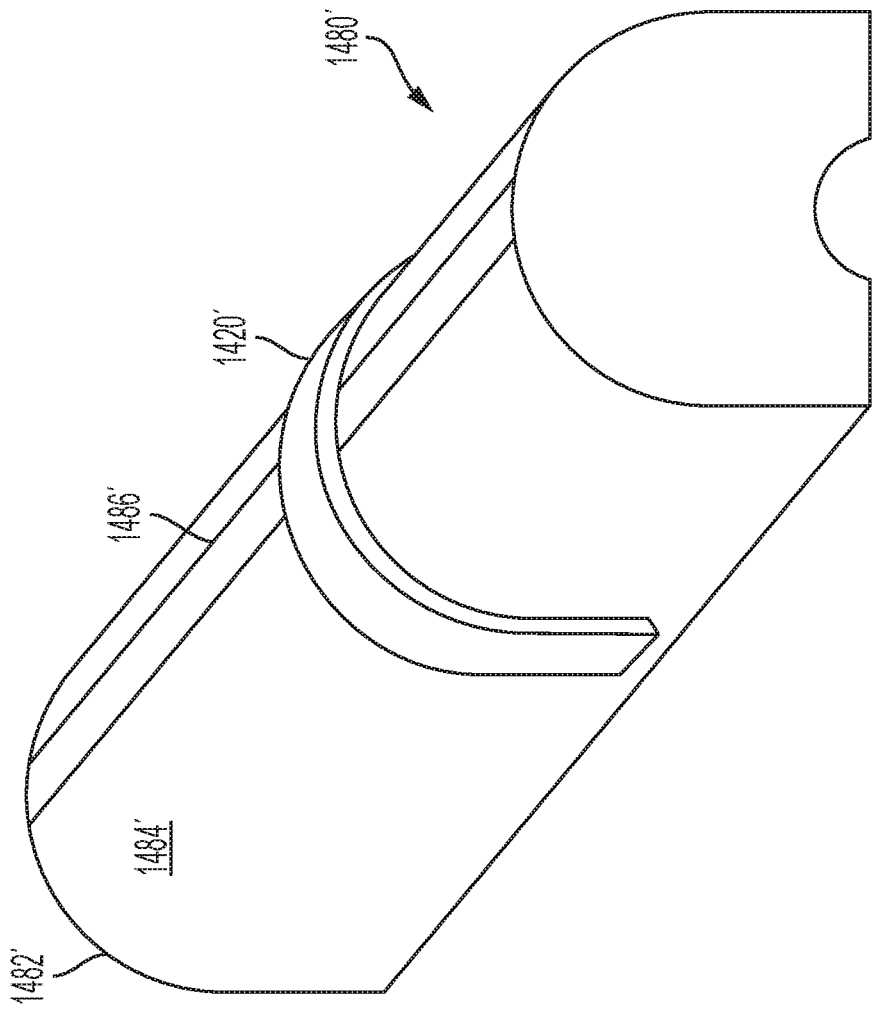
FIG. 23A depicts a perspective view of a media bath and an imaging device, according to one or more embodiments shown and described herein.

FIGS. 23A and 23B illustrate an alternative media bath 1480' including a fluid housing 1482' and ultrasound probe 1420'. In the illustrated embodiment, the fluid housing 1482' defines a curved surface 1484' over which a curved ultrasound probe 1420' travels. For example, a track 1486' may be coupled to the fluid housing 1482' at an apex of the curved surface 1484'. A linear actuator may be used to cause the curved ultrasound probe to traverse the cured surface 1484' of the fluid housing 1482'.

Referring again to FIGS. 17 and 18, the system 1300 may further include an energy source 1370 communicatively coupled to the control unit 1304. The energy source 1370 may be operatively coupled to the one more catheters via an electrical lead. The energy source 1370 may be an RF energy source to provide energy to an electrode of the treatment portion of the catheter, as described above. The one or more user input devices 1330 may be used to input commands into the control unit 1304 to excite the electrode for fistula formation. The energy source 1370 may, in some embodiments, be mounted to the moveable cart 1390.

As noted above, in some embodiments, the systems as provided herein may be used to scan a perspective anatomical region to build a venous and/or arterial 2D or 3D map and display such map on a display. For example, and as noted above, Doppler functionality may be used to allow the system to determine arterial and venous blood flows (e.g., Doppler functions may measure flow direction, velocity, etc. to allow for determination). The control unit may execute logic to build and 2D or 3D arterial map. In some embodiments, the generated 2D or 3D map may use different colors (e.g., red/blue) to illustrate venous and/or arterial blood flow. Furthermore, when a catheter is advanced through the system it may be shown on the generated the map as it is advanced through the vasculature. Such mapping may be integrated into a larger vessel map (e.g., vessel map of entire arm, leg, body, etc.) to allow a physician to contemplate an entire anatomy of a subject to determine proper treatment locations/zones. Success of treatment may be identified or confirmed using Doppler and indicated on the 2D or 3D map. For example, where a fistula is created, Doppler functionality may be used to identify new flow between adjacent vessels to determine a fistula has been created and adjust the 2D or 3D map to illustrate the same.

In some embodiments, though not shown during vascular treatment, a guidewire having an integrated tracking sensor close to its tip may be inserted into the desired vein or artery and advanced to a target treatment location under guidance of the imaging device. The catheter may then be advanced to the target treatment location over the guidewire using the one or more location sensors as described herein, or the one or more echogenic markers or rings, the treatment portion of the catheter may be tracked and displayed using the display device in real time with or without the use of fluoroscopy.

As noted herein in various embodiments overlays may be positioned over images from the imaging device and displayed on the display to provide indications as to rotational alignment, longitudinal alignment, and distance (e.g., between blood vessels and/or catheters). Additionally, the overlays may also allow a user to determine if the treatment portion in contact with the treatment location within the blood vessel. For example, and as described in greater detail above, a biasing mechanism may be activated to bias the catheter into the correct position within the vessel to deliver treatment (e.g., form a fistula).

FIGS. 24A-24D illustrate alignment of a two catheter system, such as that described above. The catheters include a 101 first catheter advanced through a first blood vessel 1500 and a second catheter 103 advanced through a second blood vessel 1502. The first catheter 101 having a first treatment portion 110 (e.g., an electrode 106) and one or more location sensors 121A/121B positioned in close proximity to the first treatment portion 110. The second catheter 103 has a second treatment portion 116 (e.g., recess 117) and one or more location sensors 123A/123B positioned in close proximity to the second treatment portion 116. Displayed on the display 1310 is a frontal plane view of the first and second catheters 101/103 within the blood vessels 1500/1502. An indicator 1311 may be displayed on the display 1310 to indicate one or more alignment indicators. For example a longitudinal alignment indicator indicating longitudinal alignment of the first and second catheter 101/103, a proximity indicator, indicating whether the first and second catheter 101/103 are close enough to one another to deliver treatment (e.g., form a fistula), and a rotational indicator, indicating whether the first and second treatment portions 110/116 are rotationally aligned with one another.

Figure 24A:
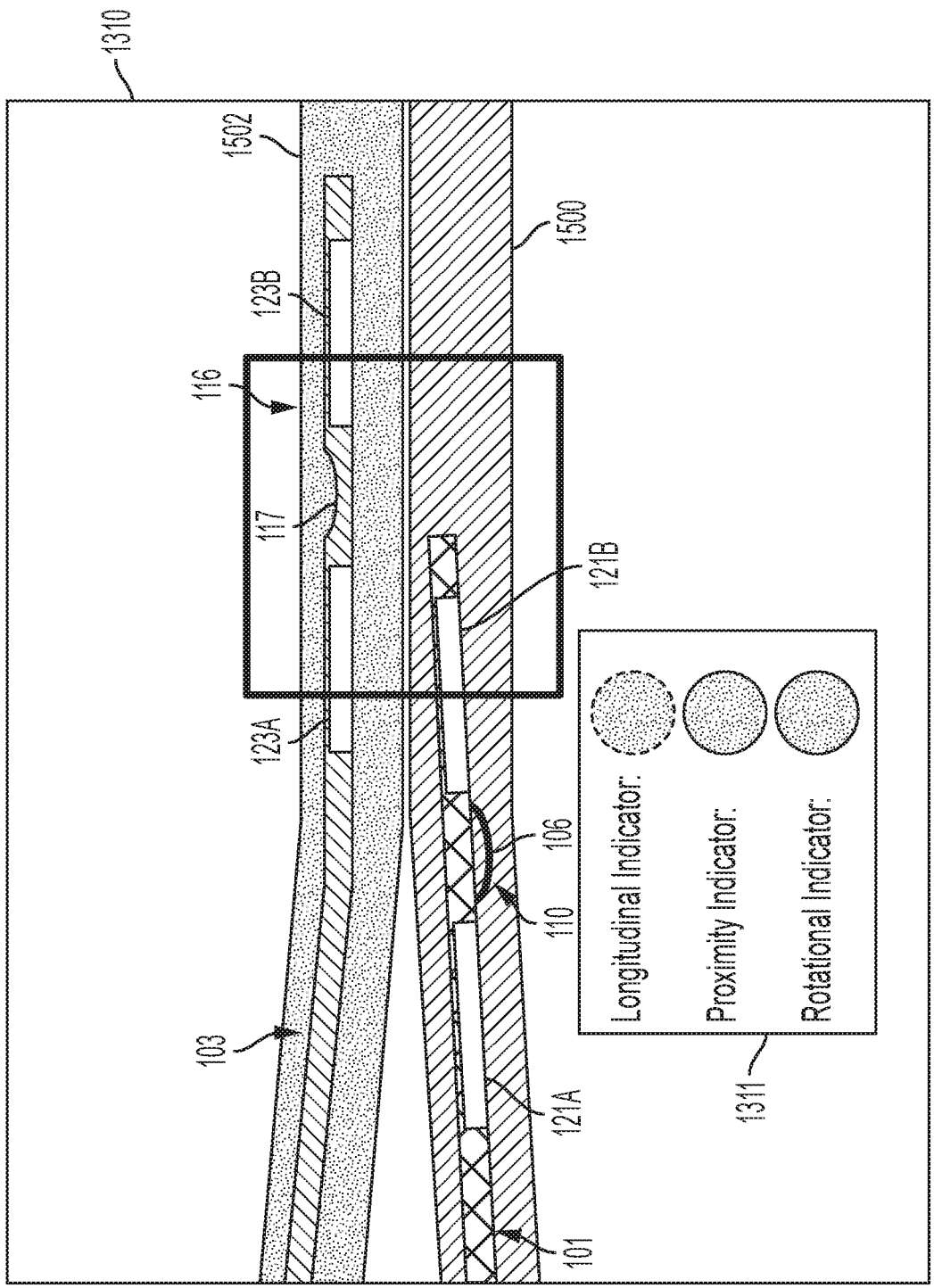
FIG. 24A depicts a display displaying imaging data from an imaging device during a vascular treatment, according to one or more embodiments shown and described herein.
Figure 24B:
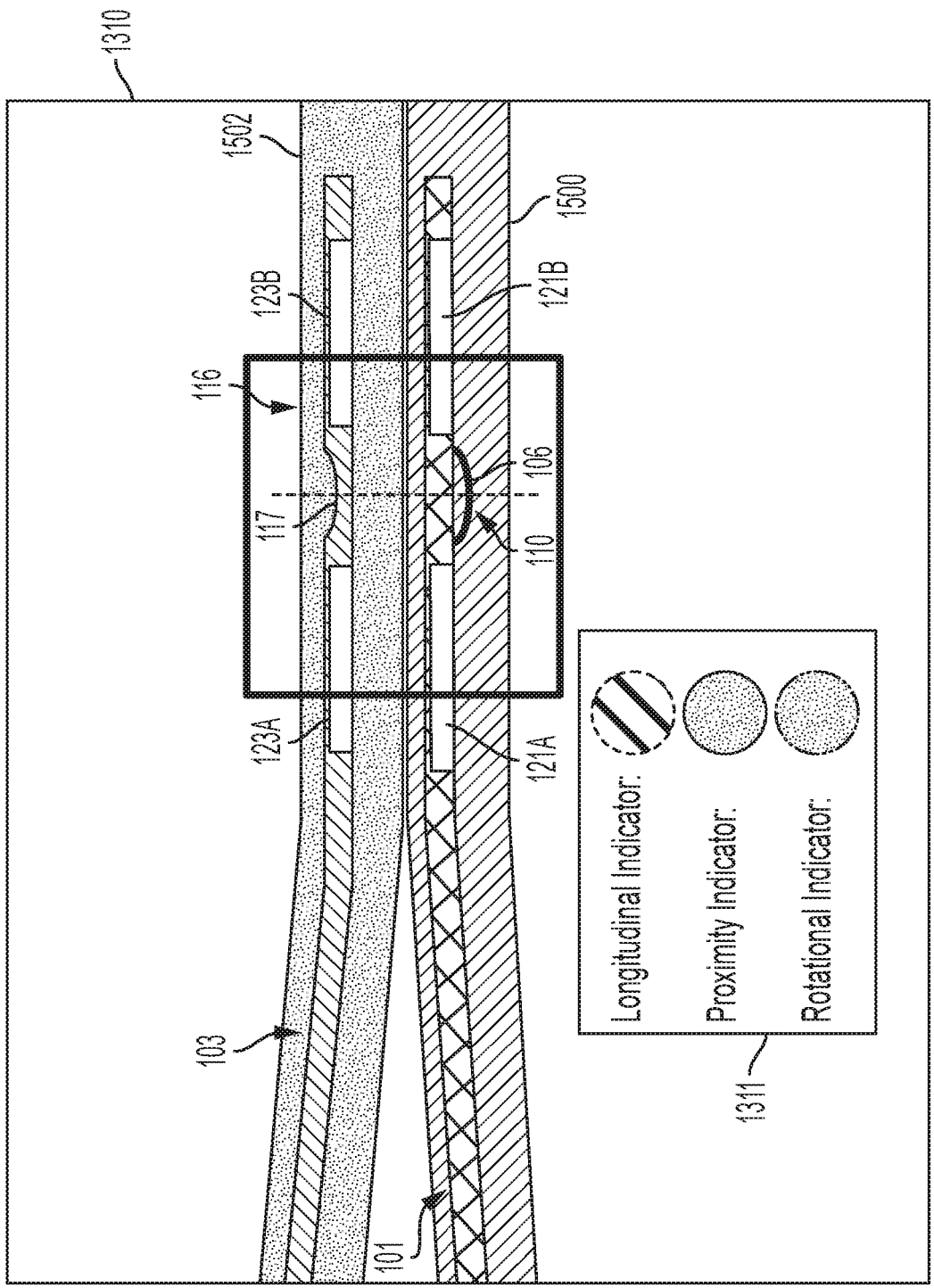
FIG. 24B depicts a display displaying imaging data from an imaging device during a vascular treatment, according to one or more embodiments shown and described herein.
Figure 24C:
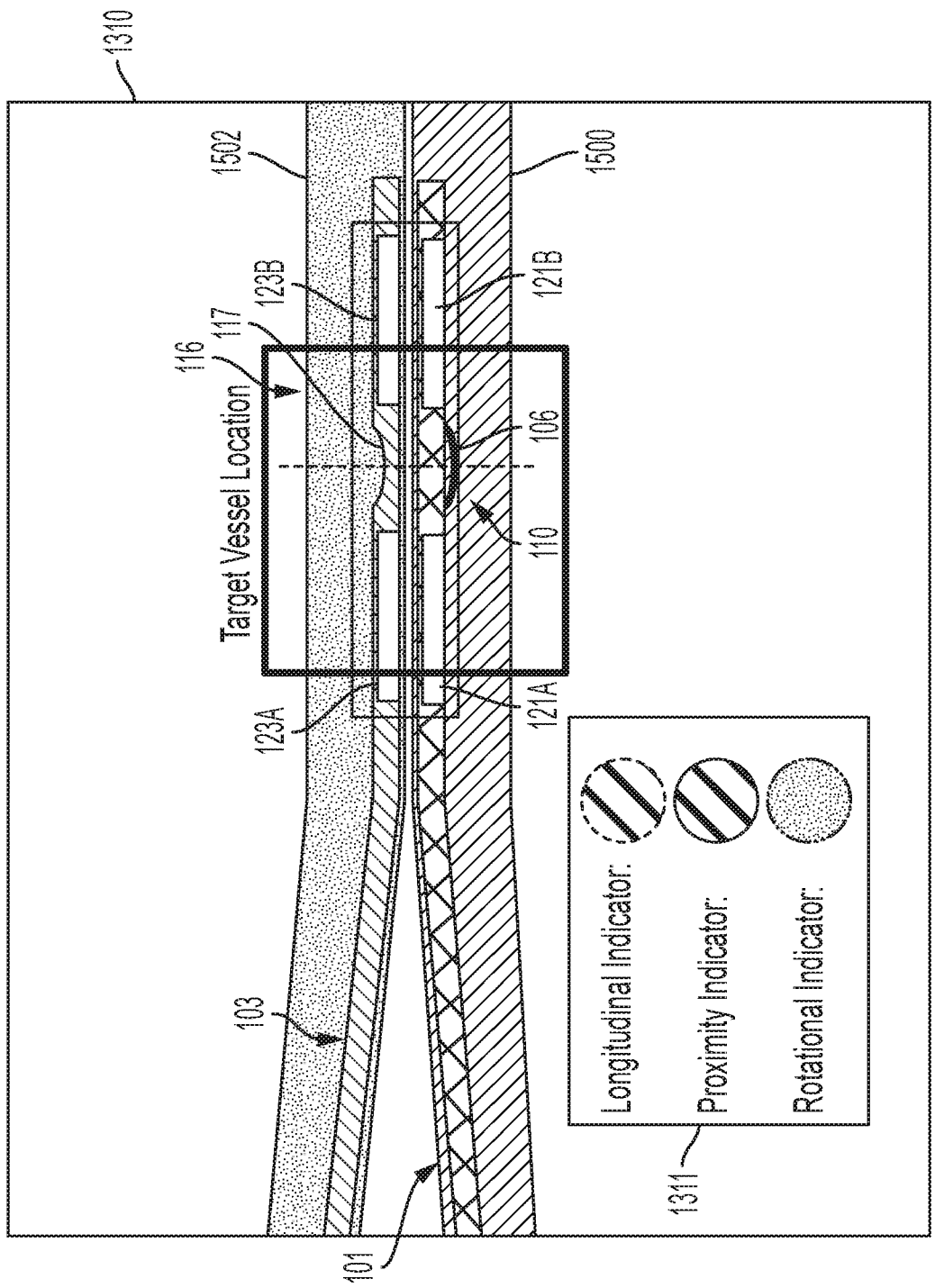
FIG. 24C depicts a display displaying imaging data from an imaging device during a vascular treatment, according to one or more embodiments shown and described herein.
Figure 24D:
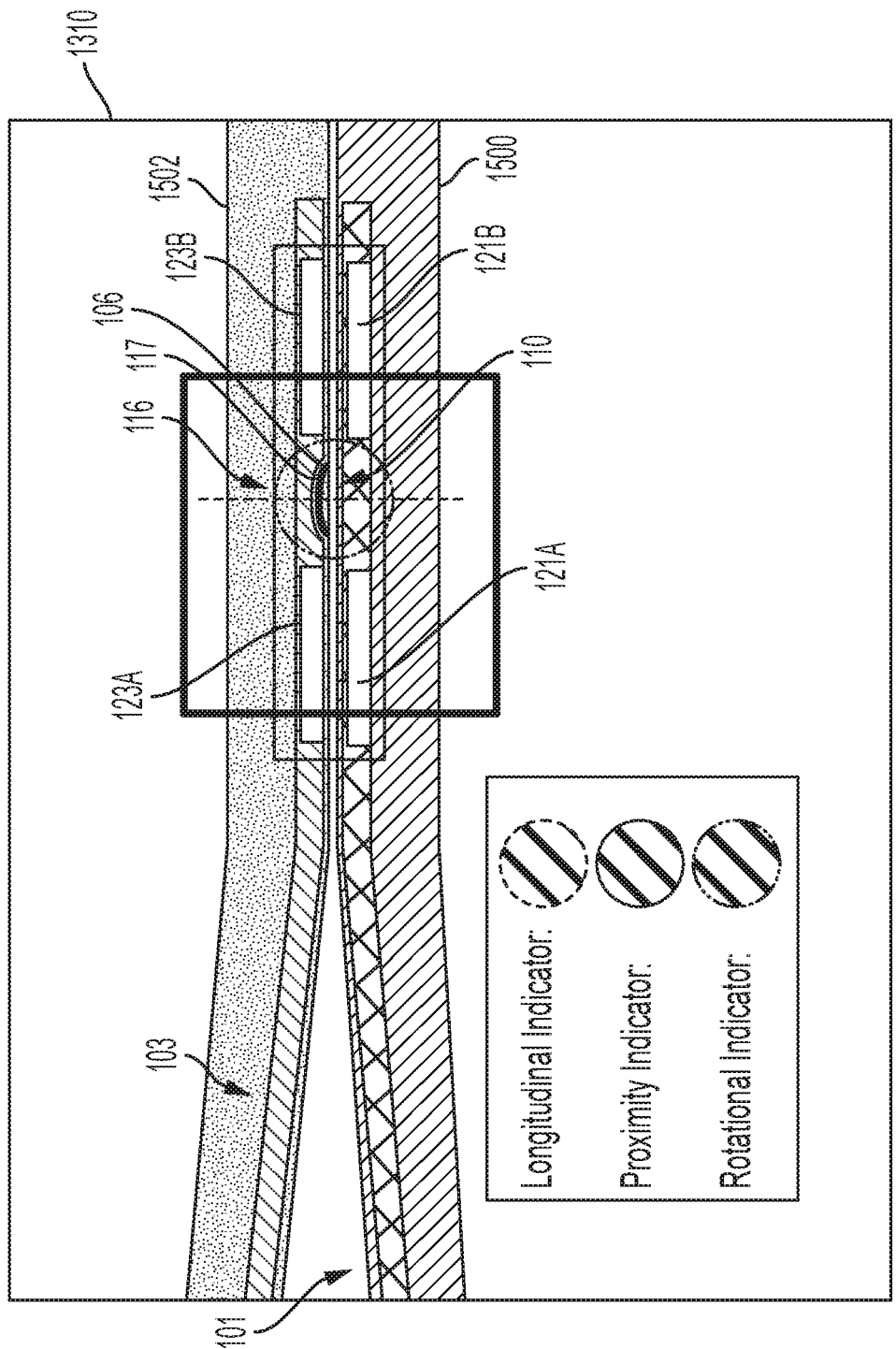
FIG. 24D depicts a display displaying imaging data from an imaging device during a vascular treatment, according to one or more embodiments shown and described herein.

In determining proximity, the control unit may track a location of each of the first and second treatment portions 110/116 based on signals from the one or more location sensors 121A/121B/123A/123B and/or the one more tracking sensors discussed above. Based on these signals, the control unit may determine whether or not the catheters are positioned within a predetermined distance such that fistula formation is position (e.g., less than 2 mm). FIG. 24B illustrates activation of the longitudinal indicator when it is determined by the control unit that the first and second treatment portions 110/116 are longitudinally aligned with one another. FIG. 24C illustrate that the first and second catheters 101/103 having been moved to a suitable proximity to one another such that a fistula may be formed. FIG. 24D illustrate that both the first catheter 101 and the second catheter 103 have proper rotational alignment such that a fistula may be formed. At this point, the electrode 106 of the treatment portion 110 of the first catheter 101 may be activated to ablate tissue sandwiched between the first treatment portion 110 and the second treatment portion 116. Doppler functionality of the imaging device may then be used to determine blood flow between the first blood vessel 1500 and the second blood vessel 1502 to confirm fistula formation.

It is noted, that the external imaging devices described herein may be similarly used for tracking and locating a single catheter system.

As noted herein, devices and methods as provided herein may be used for purposes other than fistula formation. For example, the devices as provided herein may be used for vasculature mapping purpose, arterializing purposes (e.g., arterializing a vein for ischemia in the leg), vessel occlusion, angioplasty, thrombectomy, atherectomy, crossing, drug coated balloon angioplasty, stenting (uncovered and covered), lytic therapy, etc. In addition, methods provided herein, may include multiple treatments and or multiple treatment sites.

It should now be understood that embodiments as described herein are directed the systems, methods, and catheters for endovascular treatment of a blood vessel. In particular, embodiments as described herein include imaging devices (e.g., external or endovascular imaging devices) that provide real-time imaging of a catheter to allow an operator to quickly and efficiently determine the position and alignment of a treatment portion of a catheter. Moreover, embodiments described herein may allow for use of a single catheter for such treatment as fistula formation. Thus simplifying such procedures for operators and patients alike.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

The invention claimed is:

1. A system for endovascular treatment of a blood vessel, the system comprising:
   a control unit;
   an ultrasound device communicatively coupled to the control unit, the ultrasound device comprising an ultrasound probe comprising a subject contact surface;
   a display communicatively coupled to the control unit;
   an actuator coupled to the ultrasound probe and operable to move the subject contact surface of the ultrasound probe relative to a treatment zone of a subject; and
   a catheter comprising a treatment portion, said treatment portion comprising a cutting device extending radially from said catheter;
   wherein the control unit is configured to:
      determine a position of the treatment portion of the catheter as the catheter is advanced through the blood vessel;
      move the subject contact surface of the ultrasound probe relative to the treatment zone of the subject with the actuator to follow the position of the catheter as the catheter is advanced through the blood vessel;
      use the display to display a plurality of real-time ultrasound images of the catheter as the catheter is advanced through the vessel;
      determine a radial orientation of the cutting device of the catheter within the vessel; and
      output an indicator of the radial orientation of the cutting device on the plurality of real-time ultrasound images.

2. The system of claim 1, further comprising one or more user input devices communicatively coupled to the control unit, wherein the control unit is further configured to:
   receive user input from the one or more user input devices; and
   switch to a manual operation mode from an automatic following mode to allow for manual control of movement of the ultrasound probe based on user input received by the one or more user input devices.

3. The system of claim 1, wherein the ultrasound device is a 3D ultrasound device and the control unit is configured to display two or more ultrasound images of the plurality of real-time ultrasound images including a frontal plane ultrasound image, an axial plane ultrasound image, and a sagittal plane ultrasound image.

4. The system of claim 1, wherein the ultrasound device is a 3D ultrasound device and the control unit is configured to recognize one or more vessels within the plurality of real-time ultrasound images of the ultrasound device and display a 3D model of the one or more blood vessels on the display.

5. The system of claim 1, further comprising a media bath configured to be placed over the treatment zone of the subject, wherein the ultrasound device moves within the media bath.

6. The system of claim 5, wherein the media bath comprises a flexible subject interface, wherein the flexible subject interface conforms to a shape of the treatment zone of the subject.

7. The system of claim 5, wherein the media bath comprises a housing comprising a track, wherein the ultrasound device is moveable along the track.

8. The system of claim 1, wherein the catheter further comprises a housing and a biasing mechanism coupled to the housing of the catheter and configured to bias the cutting device against a wall of the blood vessel.

9. The system of claim 8, wherein the biasing mechanism is a balloon.

10. The system of claim 8, wherein the biasing mechanism is an expandable cage.

11. The system of claim 8, wherein the biasing mechanism comprises one or more expandable wires moveable between a collapsed position and an expanded position wherein at least a portion of the one or more expandable wire are spaced from an outer wall of the housing of the catheter.

12. The system of claim 8, wherein the catheter comprises one or more echogenic markers, wherein the one or more echogenic markers indicate a rotational alignment of the cutting device of the catheter.

\* \* \* \* \*